US010228334B2

(12) United States Patent
Roe et al.

(10) Patent No.: US 10,228,334 B2
(45) Date of Patent: Mar. 12, 2019

(54) ADAPTIVE MODULAR CARGO SCREENING

(75) Inventors: Kristofer J. Roe, Port Deposit, MD (US); Timothy S. Norton, Maryville, TN (US); Nicolas Dumay, Dampierre (FR)

(73) Assignee: Smiths Detection Group Limited, Herts (GB)

( * ) Notice: Subject to any disclaimer, the term of this patent is extended or adjusted under 35 U.S.C. 154(b) by 578 days.

(21) Appl. No.: 13/577,060

(22) PCT Filed: Feb. 15, 2011

(86) PCT No.: PCT/US2011/024911
§ 371 (c)(1),
(2), (4) Date: Mar. 5, 2013

(87) PCT Pub. No.: WO2011/103097
PCT Pub. Date: Aug. 25, 2011

(65) Prior Publication Data
US 2013/0156156 A1 Jun. 20, 2013

Related U.S. Application Data

(60) Provisional application No. 61/305,128, filed on Feb. 16, 2010.

(51) Int. Cl.
G01N 23/10 (2018.01)
G01N 23/02 (2006.01)
G01V 5/00 (2006.01)

(52) U.S. Cl.
CPC ............. *G01N 23/02* (2013.01); *G01N 23/10* (2013.01); *G01V 5/0033* (2013.01);
(Continued)

(58) Field of Classification Search
CPC ............. G01N 23/10; G01N 2223/306; G01N 2223/321; G01N 2223/601;
(Continued)

(56) References Cited

U.S. PATENT DOCUMENTS 5,182,764 A * 1/1993 Peschmann et al. ........... 378/57
5,367,552 A * 11/1994 Peschmann ..................... 378/57
(Continued)

FOREIGN PATENT DOCUMENTS

WO  WO 2006/082521 A2  8/2006
WO  WO 2008/118568 A2  10/2008
WO  WO 2009/143169 A1  11/2009

OTHER PUBLICATIONS

International Search Report from the United States Patent Office for International Application No. PCT/US2011/024911, dated Apr. 18, 2011.

*Primary Examiner* — Thomas R Artman
(74) *Attorney, Agent, or Firm* — Finnegan, Henderson, Farabow, Garrett & Dunner, LLP

(57) ABSTRACT

The present disclosure is directed to systems and methods for scanning an object of interest. The system can include a controller for generating scan instructions. The system can further include a scanner, responsive to the scan instructions, for providing radiation at an energy to generate scan data for the object of interest and an other scanner, responsive to scan instructions from the controller generated based on the scan data, for providing radiation an at other energy to generate scan data for the object of interest. The system can also include a conveyance controller for generating conveyance instructions to control the relative movement of the scanner and the other scanner with respect to the object of interest based on the scan data.

31 Claims, 37 Drawing Sheets

(52) U.S. Cl.
CPC . *G01N 2223/639* (2013.01); *G01N 2223/643* (2013.01); *G01N 2223/66* (2013.01)

(58) Field of Classification Search
CPC ....... G01N 2223/633; G01N 2223/639; G01N 2223/643; G01N 2223/66
See application file for complete search history.

(56) References Cited

U.S. PATENT DOCUMENTS

| | | | |
|---|---|---|---|
| 5,600,700 A * | 2/1997 | Krug et al. | 378/57 |
| 5,870,449 A | 2/1999 | Lee et al. | |
| 5,974,111 A * | 10/1999 | Krug et al. | 378/57 |
| 7,366,282 B2 * | 4/2008 | Peschmann | 378/57 |
| 7,486,769 B2 * | 2/2009 | Brondo, Jr. | G01V 5/0069 378/57 |
| 2003/0231739 A1 | 12/2003 | Rosner | |
| 2007/0263767 A1 * | 11/2007 | Brondo, Jr. | G01V 5/0069 378/57 |

\* cited by examiner

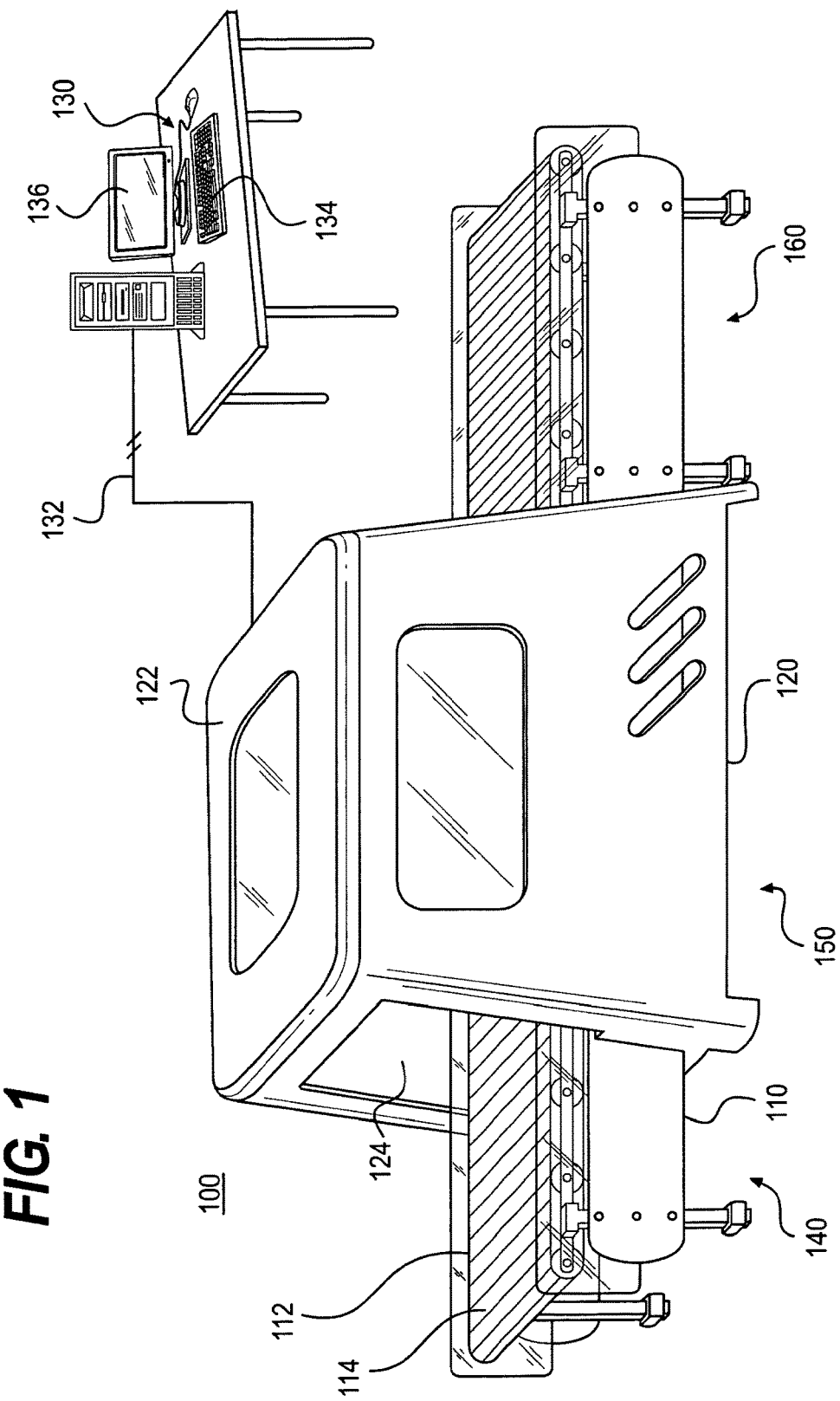

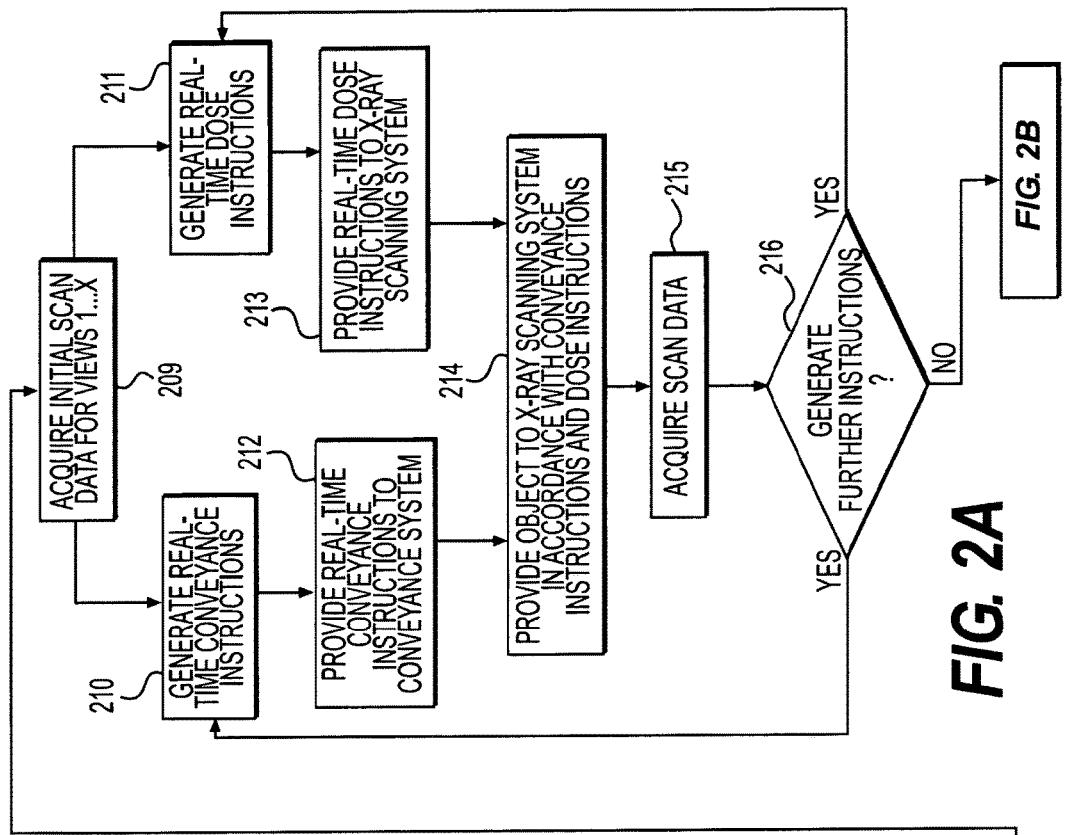
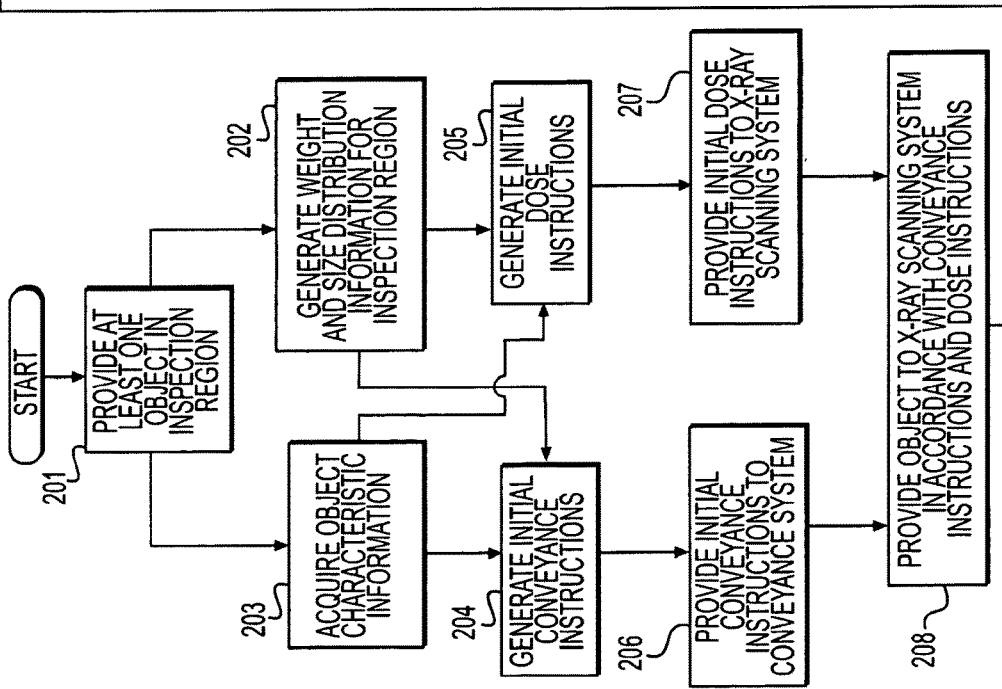
FIG. 2A

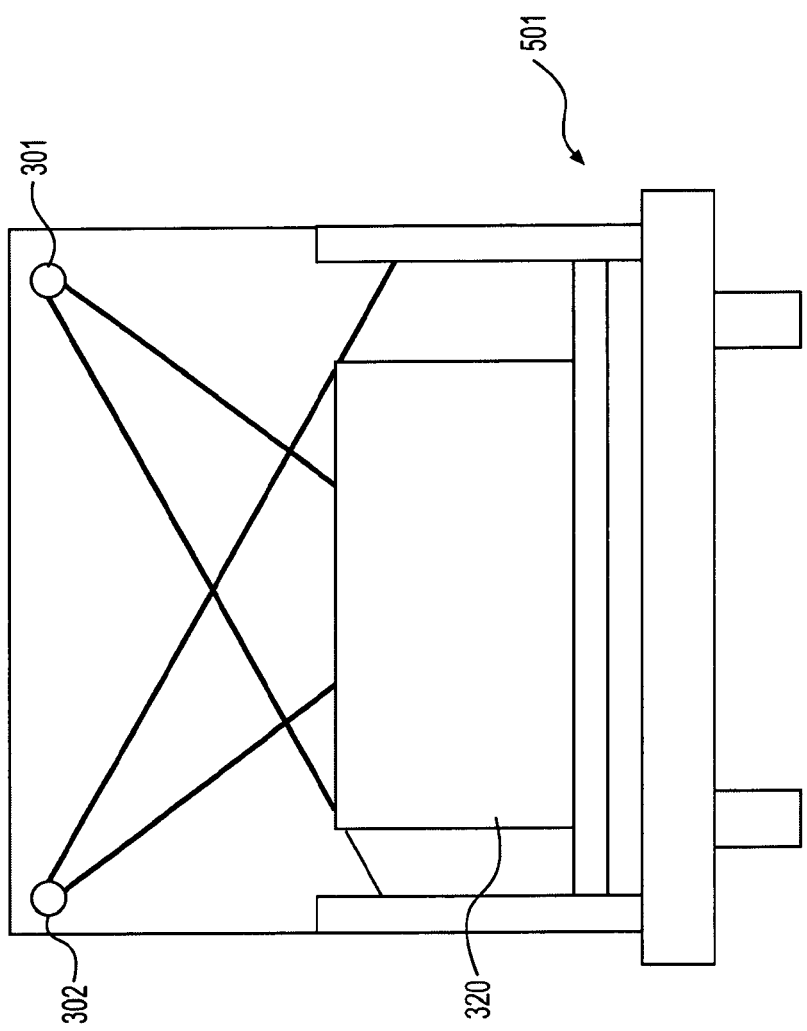

ADAPTIVE MODULAR CARGO SCREENING

RELATED APPLICATION

This application claims the benefit of priority under 35 U.S.C. § 119(e) of U.S. Provisional Application No. 61/305,128, filed on Feb. 16, 2010, the disclosure of which is incorporated herein by reference.

FIELD

The present disclosure relates generally to systems and methods for cargo inspection, more particularly, to adaptive x-ray cargo scanning.

BACKGROUND

X-ray inspection systems can be used for screening objects, such as cargo pallets, crates, and containers, to detect the presence of explosives and other prohibited items. Scanning containers, for example, can allow the contents to be examined in a non-invasive manner, i.e., without opening or physically inspecting the container.

In an x-ray scanning system, x-rays can be directed at the object in question. Depending on the density and composition of the object, some of the energy carried by the x-rays can be deposited in or reflected by the object, the energy thereby failing to be transmitted through the object being referred to as absorbed energy, or the absorbed dose. Transmitted x-rays can then be measured by a detector located proximate to the object and opposite the x-ray source. Among other factors, the attenuation of the transmitted radiation can be a function of the density of the material being scanned. Data received by the detector can be used to produce a radiographic image that that can be correlated with the shape, size, and density of the scanned object.

In addition, data received at the detector can be used to determine an absorption coefficient and effective atomic number of materials associated with the scanned object. Materials of interest, including, for example, explosive materials can be identified by comparing the absorption coefficients of the acquired data with known absorption coefficients of known materials of interest.

Both the size and density of the scanned object can affect the resultant x-ray data. The contents of containers scanned in a shipping setting, for example, can vary widely in both density and composition. For example, x-ray scanning systems that use the same total emitted radiation, i.e., high-energy or low-energy, regardless of the object being scanned, can generate data or images of poor quality that cannot be used to accurately identify items of interest.

In general, "low-energy" x-ray scanning systems can operate within the energy range of 75 kV to 200 kV. Due to the low power of these sources, inspection can be limited to small, low-density containers, such as those containing, for example, mail, flowers, or clothing. "High-energy" scanning systems, those that can generally operate in the range of 300 kV to 10 MV, can be used to inspect larger, higher-density items and containers, such as those containing, for example, machine components, construction materials, or electronics. Therefore, a low-energy scanner can exhibit insufficient x-ray penetration to effectively screen high-density objects. Similarly, a high-energy scanner, can fail to produce an adequate image of a low-density object.

SUMMARY

In one aspect, the present disclosure is directed to a system for scanning an object of interest. The system can include a controller for generating scan instructions. The system can further include a scanner, responsive to the scan instructions, for providing radiation at an energy to generate scan data for the object of interest. The system can also include an other scanner, responsive to the scan instructions, for providing radiation at an other energy to generate other scan data for the object of interest. The system can also include a conveyance controller for generating conveyance instructions to control the relative movement of the scanner and the other scanner with respect to the object of interest based on the scan data and the other scan data.

An additional aspect of the present disclosure is directed to system configured to scan an object of interest. The system can include a controller that generates scan instructions based at least in part on input data and generates other scan instructions based on scan data. The system can also include a scanner, responsive to the scan instructions, for providing radiation at an energy to the object of interest, and for generating the scan data associated with the object of interest. The scanner can also provide radiation at an other energy to the object of interest responsive to the other scan instructions. The system can further include a conveyance controller for generating conveyance instructions based at least in part on the input data and that generates other conveyance instructions based on the scan data, and where the conveyance instructions and the other conveyance instructions define a relative movement between the scanner and the object of interest.

An additional aspect of the present disclosure is directed to a computer-readable medium storing a program that, when executed by a processor, performs a method of scanning an object of interest. The method can include generating scan instructions, generating conveyance instructions, and providing radiation to an object of interest using a scanner at an energy in response to the scan instructions and the conveyance instructions. The method can also include acquiring scan data, evaluating the scan data and generating other scan instructions and other conveyance instructions, and providing radiation to the object of interest using the scanner at an other energy in response to the other scan instructions.

Additional objects and advantages will be set forth in part in the description which follows, and in part will be obvious from the description, or can be learned by practice of the disclosed embodiments. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1 is a schematic diagram of an inspection system consistent with an embodiment of the present disclosure;

FIGS. 3-5 illustrate a dual view radioscopic inspection system consistent with an embodiment of the present disclosure;

DESCRIPTION OF THE EMBODIMENTS

Figure 2B:
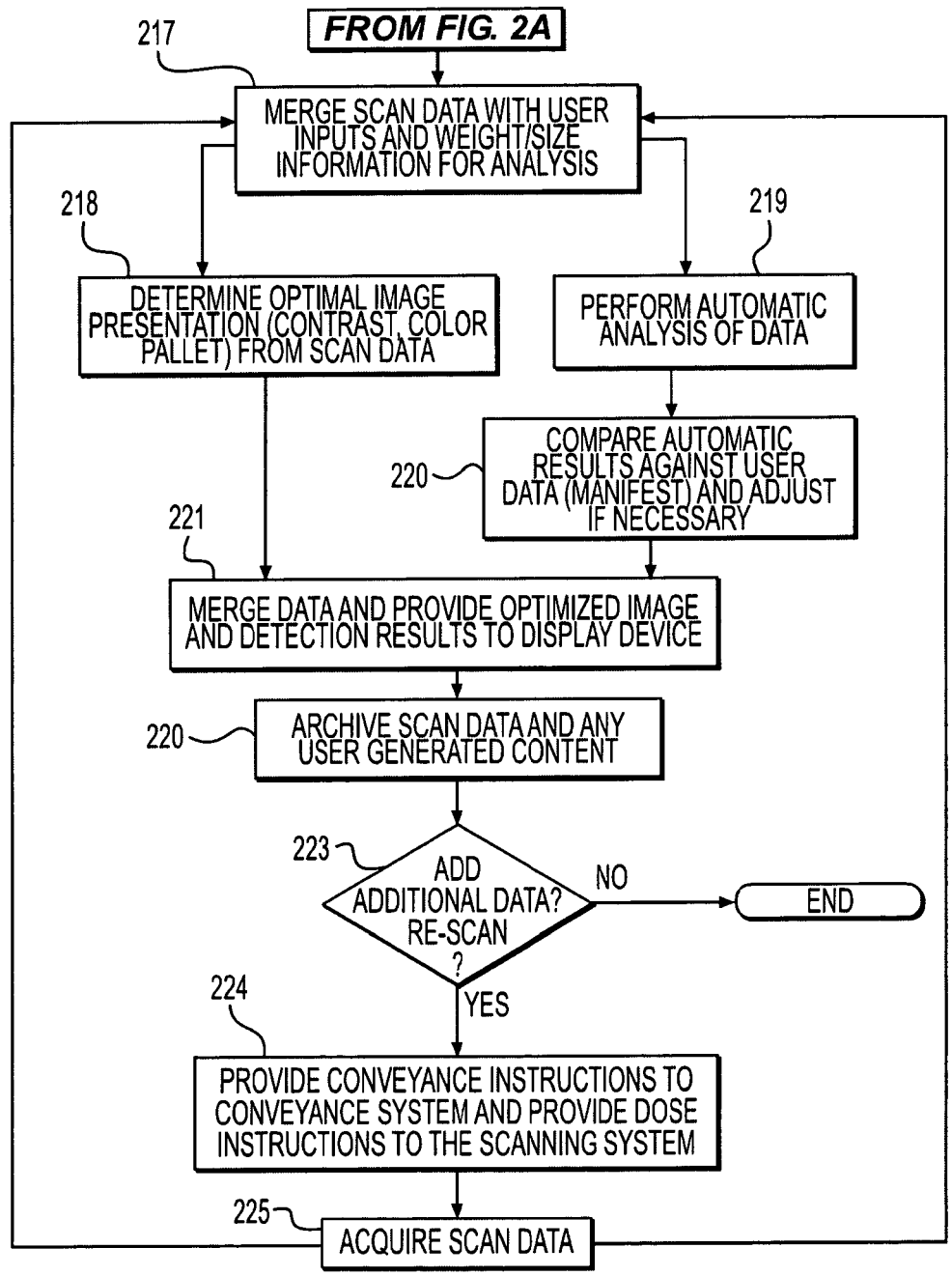
FIG. 2 is flow chart of an exemplary process of analyzing an object utilizing an inspection system, consistent with the present disclosure.

Reference will now be made in detail to embodiments including the embodiments illustrated in the accompanying drawings. Wherever possible, the same reference numbers will be used throughout the drawings to refer to the same or like parts.

FIG. 1 is a schematic diagram of an inspection system 100 according to an embodiment of the present disclosure. An embodiment of the inspection system 100 can be configured to scan an object to detect any material or object of interest that can be otherwise obscured from view or concealed. For example, the object may be a container, crate, bag, box, cargo pallet, truck, car, van, bus, trains, or other cargo container used in the shipping or delivery of goods. The object can be one that is transported by truck, airplane, sea vessel, train, or other mode of conveyance. The object can contain any plurality of objects, such as, for example, commercial consumer goods, electronic devices, machine equipment, constructions materials, etc. The object can be associated with object characteristic information, where the object characteristic information includes that which is known about the nature of the object, including, for example, conveyance type and declared contents, such as manifest data. The object can contain an object of interest, such as a (but not limited to) weapon, e.g. a gun or knife, incendiaries, narcotics, radioactive materials, or explosives, such as, but not limited to a bomb, improvised explosive device, liquid explosive material, plastic explosives, and the like. As indicated above, the object of interest can also be anything contained in the object, such as, for example, commercial consumer goods, electronic devices, machine equipment, construction materials, etc. In one embodiment, the inspection system 100 can be employed at a port of import or border control to scan and/or detect objects of interest or materials in the object. It is contemplated that the inspection system 100 can be employed to scan and/or detect any object of interest or material in any item capable of being scanned and/or detected. The object also can include illegal consignments inside trucks, van, cars, and sealed containers for customs applications.

The inspection system 100 can include a conveyance system 110, an x-ray scanning system 120, and a data processor 130 coupled to the conveyance system 110 and the x-ray scanning system 120.

The conveyance system 110 can include a conveyor 112, a weight and size measurement system (not shown), a distribution analyzer (not shown), and a conveyance controller (not shown). The conveyance controller will be capable of variable operation in real time. As used herein, the noun "real time," in connection with a scanned object and a scanning system, means a time interval that is shorter than or approximately equivalent to the time interval required to convey the object through the scanning system (such a time interval consistent with the present disclosure, for exemplary purposes only, and without limitation, can be within a range from milliseconds to a few seconds). The conveyor 112 can include belts 114 and/or rollers for supporting the object and one or more motors to the drive belts 114 and/or rollers. The belts 114 and/or rollers can operate intermittently or continuously to convey or provide the object from a loading area 140, through an x-ray scanning area 150, to an unloading area 160. It is contemplated that other forms of conveyors can be used. The conveyor 112 can be configured to vary the direction, speed, and acceleration of the motor and associated belt in accordance with instructions received from the conveyance controller and/or the data processor 130.

The weight and size measurement system can include scales or sensors for measuring properties of the object, such as weight, size, density, and distribution of the object, in one, two, or three dimensions. As used herein, the region which remains relatively fixed with the object being scanned is referred to as the inspection region. Such a region, for example, can be visualized as a region that is fixed relative to a conventional four foot by five foot cargo pallet. The weight and size measurement system can take measurements of the inspection region in real time. It is contemplated that other methods of weight and size measurement can be used. The distribution analyzer, using weight and size information associated with the object (or the scanning region), can be configured to generate distribution information associated with the object. The distribution analyzer can be configured to define an inspection region associated with an object or region of the object of particular interest and that identifies the area to be scanned by the x-ray scanning system 120. The inspection region can include the entire object or a portion of the object. The inspection region can be defined in one, two, or three dimensions. The distribution information associated with the object can comprise weight/mass distribution information as a function of the inspection region. In an embodiment, the distribution analyzer can use weight and size information to determine the weight distribution of the object. This analysis can be accomplished in real time.

The conveyance system 110 can also include a conveyance controller configured to accept the distribution information and the object characteristic information associated with the object and/or inspection region, and generate initial conveyance instructions for the conveyor 112. The initial conveyance instructions can include, for example, instructions to vary the speed and/or acceleration of the conveyor 112 through the x-ray scanner 122. As used herein, the region (or regions) that remain fixed relative to the x-ray scanning system 120 and that is (or are) subject to the applied radiation is referred to as the "scanning region." In an exemplary embodiment, by defining the conveyor speed and/or acceleration, the initial conveyance instructions can influence the initial x-ray dose and scanning speed of the object through the scanning region (or regions).

The conveyance controller can also be configured to analyze the data from the x-ray scan of the object. The conveyance controller can further be configured to generate updated conveyance instructions for the conveyor 112. The conveyor 112, in response to the initial conveyance instructions and the updated conveyance instructions can be configured to vary the speed of the object through the x-ray scanning system 120. The analysis of the x-ray data can occur in real time and, thus, can provide real-time updated conveyance instructions.

The x-ray scanning system 120 can include an x-ray scanner 122 and a scanner controller. The x-ray scanner 122 can be configured to apply x-ray beam(s) of radiation to the object or inspection region, in accordance with instructions received from the scanner controller and/or the data processor 130. In one embodiment, the scanner controller can perform analysis and generate instructions including adapted instructions, in real time. The x-ray scanning system 120 can also, actively or passively, examine the object and/or inspection region for radioactive material, gamma radiation, and/or neutron detection. For example, the x-ray scanning system 120 can be configured to detect radioactive potassium-based items as an object of interest within the scanned object.

It is contemplated that multiple x-ray scanners 122, of varying energies, can be used within the x-ray scanning system 120. The disclosed x-ray scanning system 120 can include both a high-energy scanner suitable for scanning high density objects and a low-energy scanner suitable for scanning low-density objects. For example, an exemplary embodiment of the x-ray scanner 122 can include a first x-ray scanner, such as a linear accelerator, and a second x-ray scanner, such as a 140-kV x-ray generator. The disclosed x-ray scanning system 120 can also include a scanner 122 which is capable of dynamic control over dose and/or acceleration voltage to screen objects at varying dose and penetration profiles. For example, the x-ray scanning system 120 can implement variable dose and penetration profiles on a single object. As illustrated by an embodiment, the x-ray scanning system 120 can scan a first inspection region of the object at a first energy and second inspection region of the object at a second energy, where the first energy and the second energy are different. As used herein, the phrases "low-energy" and "high-energy" both refer to energy ranges that lie generally between 75 kV and 10 MV, where "low-energy" and "high-energy" refer to the relative voltage only, being relatively "low" and "high" respectively. For example, it is contemplated, without limitation, that both "low-energy" and "high-energy" can lie generally in the MV range.

It is also contemplated that the various x-ray scanners 122 can be modular and/or can comprise modular components, allowing for ease of replacement of defective or damaged components. The x-ray scanning system 120 can have a small or compact footprint. Particularly, it is contemplated that the low-energy x-ray scanner(s) can be utilized for side-view applications, and the high-energy x-ray scanner(s), which are usually larger, can be utilized for top-view application, thereby providing an x-ray scanning system 120 with a compact x-y footprint. For example, in an embodiment, a high-energy X-band linear accelerator can be used for the top-view and a low-energy 140-kV x-ray generator can be used for the side-view. A further embodiment of the x-ray scanning system 120 provides for multiple x-ray scanners 122 located above the object, allowing for dual x-ray transmission views of the object and also providing a compact footprint.

In an embodiment, the x-ray scanner 122 can include, among other things, an x-ray source and an x-ray detector. The x-ray source and the x-ray detector can be mounted, stationary, on opposite sides of an aperture 124 through which the object can be conveyed. The aperture 124 can be of any suitable shape, including, without limitation, circular, square, oval, or U-shaped. It is contemplated that the aperture 124 can be configured to accommodate conventional four foot by five foot shipping pallets and/or conventional shipping containers such as standard LD3 and/or LD7 unit load device (LD) containers.

The x-ray source can generate x-ray beam radiation over a substantially two-dimensional cross-section through which the object passes. The energy associated with the x-ray beam can travel along a direction within a plane defined by the x-ray detector. X-ray beams can be generated over a continuous range of energies, and can be generated by multiple x-ray sources or by a single source that operates in a switched manner. In an embodiment, there is a one-to-one relationship between x-ray sources and detectors (i.e., two sources and two detectors). It also is contemplated that the x-ray scanner 122 can be implemented with any number of movable or rotatable sources and/or detectors in a one-to-many or many-to-one relationship to illuminate the object.

After the x-ray beam passes through, and is partially attenuated by, the object, the x-ray beam can be received by the x-ray detector. As used herein, the radiation data acquired by the x-ray detector is referred to as "projection data," and the perspective defined by the uniform cross-section intersecting with the scanned item is referred to as a "projection perspective." During a scan, the x-ray detector can collect multiple sets of projection data representative of the integral of absorption coefficients of the volumetric segment of the object through which the x-ray beams pass. A measurement of projection data can form a raster line of a two-dimensional projection image. As the object passes through the x-ray scanner 122, a two-dimensional projection image can be formed as a function of the x-ray energy from the two-dimensional projection data acquired at that energy value.

The x-ray scanning system 120 can also include a scanner controller configured to analyze the distribution information associated with the inspection region and the object characteristic information associated with the object and determine an initial dose instruction. The initial dose instruction can be sent to the x-ray scanner 122 and the dose of the initial x-ray radiation beam can be adjusted accordingly. Upon applying the initial x-ray radiation beam in accordance with the initial dose instruction, the x-ray scanner 122 can be configured to acquire initial scan data associated with the inspection region.

The scanner controller can be further configured to analyze scan data and generate updated dose instructions for the x-ray scanner 122. The x-ray scanner 122, in response to the initial dose instructions and the updated dose instructions, can be configured to vary a dose of the radiation applied to the inspection region. In one embodiment, the scanner controller is a real-time scanner controller and the scan data can be analyzed in real-time and the updated dose instructions generated in real-time.

A data processor 130 can be coupled to the conveyance system 110 and the x-ray scanning system 120 via, for example, one or more data transmission lines 132. The multi-energy projection data acquired by the x-ray scanner 122 can be transferred to the data processor 130 via data transmission lines 132. In one embodiment, the projection data can be wirelessly transferred to the data processor 130 to enable, for example, a remote screening application or a cloud networked application.

The data processor 130 can include one or more computer assemblies configured to detect an object of interest and/or radioactive material in an object based on scan data received from the x-ray scanner 122. The data processor 130 can be associated with one or more software applications, including, for example, an image analysis and/or reconstruction tool and/or a material classification tool. These software applications can be stored on the data processor 130, and can be accessed by a user, such as, for example, an operator at a customs inspection point at a seaport or airport. The software applications can also be stored on a computer readable medium, such as, without limitation, a hard drive, computer disk, CD-ROM, or any other suitable medium.

The data processor 130 can include a processor, a memory module, a scanner control interface, a conveyor control interface, a storage device, an input/output interface 134, and a display device 136. The data processor 130 can include additional, fewer, and/or different components than those listed above. The type and number of listed components are provided for the purpose of listing examples and are not intended to be limiting.

The processor can be a central processing unit(s) (CPU) and/or a graphic processing unit(s) (GPU). The processor can execute sequences of computer program instructions to perform various computation and analysis processes. The memory modules can include, among other things, a random access memory (RAM) and a read-only memory (ROM). The computer program instructions can be accessed and read from the ROM, or any other suitable memory location, and loaded into the RAM for execution by the processor. Depending on the type of data processor 130 being used, the processor can include one or more printed circuit boards, and/or a microprocessor chip, or may have the form of a multi-processor industrial computer or a combination of several independent rack computers optimized for different processing tasks such as image analysis, detection algorithm processing, and image presentation.

The scanner control interface can be configured for two-way communication between the x-ray scanning system 120 and the data processor 130. In an embodiment, the scanner control interface can be configured to receive scan data from the x-ray scanning system 120 and store the data onto a storage device. The scanner control interface can also be configured to send dose instructions to the x-ray scanning system 120 to initiate, stop, or otherwise configure the x-ray scanning system 120 operations. For example, dose instructions can include scan configuration parameters, such as, designating the energy level to be used for a particular x-ray scan.

The conveyor control interface can be configured for two-way communication between the conveyance system 110 and the data processor 130. In an embodiment, the conveyor control interface can be configured to receive conveyor and/or object information from the conveyance system 110 and store the data on a storage device. The conveyor control interface can also be configured to send conveyance instructions to the conveyance system 110 to initiate, stop, or otherwise modify the operations of the conveyance system 110. For example, conveyance instructions can include parameters for conveyor 112 or the distribution analyzer, such as, speed settings for the conveyor 112 or user-defined target region information.

It is also contemplated that the data processor 130 can provide instructions to the x-ray scanning system 120 and the conveyance system 110, via the scanner control interface and the conveyor control interface, to operate the inspection system 100 in various operating modes, including, for example, a mobile mode, a pass-through mode, and a high performance mode. The mobile mode can include the inspection system 100 configured, for example, mounted on a truck, trailer platform, or other portable structure suitably designed to provide adequate support and radiation shielding. In mobile mode, the inspection system 100 can include additional image processing features to accommodate for source and detector movement during x-ray scanning. It is contemplated that in mobile mode, an exemplary embodiment of the x-ray scanning system 120 can include one x-ray scanner 122 located above or higher than the object, and a low-energy x-ray scanner can be located to provide a side view of the object. In this manner, the mobile mode of the inspection system 100 can provide multiple-view x-ray transmissions of the object in a relatively lightweight and compact configuration.

A pass-through mode can include an inspection system 100 configuration where the object to be inspected travels under its own command through the inspection system 100. For example, in pass-through mode, a flat-bed truck and its associated cargo may be driven by a driver through the inspection system 100. It is also contemplated that the control of the object through the inspection system 100 is regulated or controlled to prevent driver/operator irregularities. Pass-through mode can be used when low density cargo is being screened, thus allowing the x-ray scanning system 120 and the conveyance system 110 to operate at high efficiency without compromising accuracy. During pass-through scanning, objects can be screened for the presence of radiological material and to identify areas of interest for additional screening. High-performance mode can provide individual customized scanning as provided by the present disclosure.

The data processor 130 also can visually display information to the user via a display device 136. The display device 136 can include, for example, a computer screen that provides a graphical user interface (GUI) to the user. Consistent with an embodiment, the display device 136 can display a scan image of the object, such as, for example, a two-dimensional projection image of the target region. The scan image can depict different colors or contrast to indicate the x-ray absorption and/or effective atomic number of various portions of the target region. The data processor 130 can identify areas within the target region that were not capable of sufficient resolution due to insufficient x-ray beam penetration based upon scan data received from the x-ray scanning system 120. For example, the data processor 130 can provide the user with an insufficient penetration notification and/or automatically highlight portions of the scan image that have limited information or quality. Based on user input regarding the target region and/or the identified region of insufficient x-ray beam penetration, the data processor 130 can adjust the conveyance instruction and the scan instruction, either automatically or in response to operator instructions.

The data processor 130 can also normalize scan data received from various x-ray scanners 122. Particularly, it is contemplated that the data processor 130 can receive projection data from multiple x-ray scanners 122. Multiple x-ray scanners 122 can interrogate different views of the object and/or obtain data at different x-ray energies. The data processor 130 can analyze the scan data to determine size and measurement information such where such information is unavailable from the weight and size measurement system or identify congruence with the size and measurement information received from the weight and size measurement system. The data processor 130 can analyze the data to form a composite three-dimensional scan image representative of the inspection region and perform independent analyses of the individual two-dimensional projections. In one embodiment, the data processor 130 can include automatic shape and pattern analysis features. Scan data and images can be compared to a database including information on known objects of interest, including radioactive materials. If the scan data and/or image correlates with or closely resembles data and/or an image of an object of interest, the user can be signaled and/or a notation can be recorded as to the presence of a possible object of interest. The display device 136 can also display an inspection report to the user indicating whether the scan data is consistent with the presence of a threat material within the object.

The data processor 130 can process the scan data from various x-ray scanners 122 and determine optimal image presentation parameters (color palette, contrast, etc.), it can also display on the display device 136 pertinent manifest and weight and size information. The data processor 130 can also include detection algorithms, running in parallel, that process scan image data, taking into account object characteristic information and size and weight information from the weight and size measurement system. The algorithms can prepare any results regarding detection of objects of interest and predetermined "anomaly" items. The data processor 130 can cue the user based on the comparison of the scan data with object characteristic information and present the cues and/or display notation associated with such comparison with the scan image data on the display device 136.

The storage device can include any type of mass storage suitable for storing information. For example, the storage device can include one or more hard disk devices, optical disk devices, or any other storage devices that provide data storage space. In one embodiment of the present disclosure, the storage device can store data related to the data processing process, such as the scan data received from the x-ray scanning system 120 or the conveyance system 110, and any intermediate data created during the data processing process. The storage device can also include analysis and organization tools for analyzing and organizing the information contained therein.

The data processor 130 can be accessed and controlled by a user via an input/output interface 134. The input/output interface 134 can be provided for the user to input information into the data processor 130, and can include, for example, a keyboard, a mouse, a touch screen, and/or optical or wireless computer input devices. The user can input control instructions via the input/output interface 134 to control the operation of the x-ray scanning system 120 and the conveyance system 110. The user can also make and store notes and any other data relevant to the inspection system 100. For example, the user can trigger an x-ray scan using the embodied technology of the data processor 130. Similarly, the user can manually input parameters that adjust the operation of the conveyor 112 and one or more of the x-ray scanners 122, or the user can initiate secondary "resolution" technology, such as, for example, explosive trace detection systems.

FIGS. 2A and 2B provide a flow chart of a process of analyzing an object using real-time x-ray dose control and real-time conveyance control of the object through the x-ray beam, consistent with the embodiment shown in FIG. 1. Such control can be used to increase scan efficiency and enhance image interpretation. An object suitable for scanning can be provided to the x-ray scanner by a conveyor (Step 201). The conveyor can receive the object and the weight and size measurement system can measure the weight, size, and weight distribution of the object under inspection. These size and weight measurements can consist of one-dimensional measurements or multidimensional measurements. The distribution analyzer can receive the weight and size information and based on the information generate distribution information for the associated object (Step 202). For example, the distribution analyzer can generate a weight distribution profile to identify, in two-dimensions, areas of higher a lower weight. The distribution analyzer also can use the weight and size information to define a region of interest of the object. The region of interest can include the entire object, a portion of the object, or a user-defined portion of the object, in one, two, or three dimensions.

The conveyance controller can receive the distribution information and any available object characteristic information (Step 203) and can generate initial conveyance instructions for the conveyor 112 (Step 204). In an embodiment, the conveyance controller can use the object characteristic information to identify any corresponding absorption information available for known materials identified by the object characteristic information. The conveyance controller can use the distribution information to estimate the length of the x-ray path through the object. The conveyance controller can determine the initial speed of conveyor 112 and, in turn, the initial scan speed of the object by analyzing estimated absorption information in relation to the desired x-ray beam path, i.e., distribution information. The conveyance controller can provide the initial conveyance instructions to the conveyance system 110 (Step 206).

The scanner controller can also receive the distribution information and any available object characteristic information and generate an initial dose instruction for the x-ray scanner 122 (Step 205). In an embodiment, the scanner controller can use the object information, including any corresponding absorption information, and the distribution information, including the estimated length of the x-ray path, to determine an initial x-ray dose. In one embodiment, the scanner controller can identify, based on the preliminary information, a preferred initial x-ray energy and corresponding x-ray scanner 122. The scanner controller can provide the initial dose instructions to the x-ray scanning system 120 (Step 207).

The conveyance system 110 and the x-ray scanning system 120 can provide the object to the x-ray scanner 122 in accordance with the initial conveyance instructions and initial dose instructions (Step 208). The x-ray scanner 122 can acquire initial scan data associated with the inspection region by applying the initial x-ray 122 radiation beam at various energies and in various views in accordance with the initial dose instruction (Step 209). During the x-ray scan, multiple sets of two-dimensional projection data can be acquired at multiple projections angles at multiple x-ray energies by the respective scanner and detector pairs in x-ray scanner 122. The projection data can be transferred to the data processor 130. The projection data can be reconstructed into two or three-dimensional radiographic image that represents an absorption coefficient map and/or an effective atomic number map of the object.

The initial scan data can be analyzed by the conveyance controller and the scanner controller to determine whether the target region has low, medium, or high x-ray absorption where the absorption can be normalized to unit width or distance (Step 210, Step 211). The conveyance controller and the scanner controller can provide instructions to the conveyance system 110 and the x-ray scanning system 120 to adjust the x-ray dose and scan speed in accordance with the properties of the inspection region (Step 212, Step 213). The conveyor 112, in response to the conveyance instructions can be configured to adjust the speed of the object through the target region, thereby adjusting the scan speed of the object. The x-ray scanner 122, in response to the dose instructions, can be configured to adjust the dose of the radiation applied to the target region. For example, the initial scan data can indicate that the object has a high density. The conveyance controller and the scanner controller can then adjust the scan speed and x-ray dose to accommodate the high-density object and produce scan data that provides adequate identification of any object of interest within the inspection region (Step 214). In this manner, the inspection system 100 can adjust to the properties of the object and target region under inspection and provide updated scan information adequate to produce scan images that benefit from the updated configuration (Step 215). The acquired scan data can be analyzed by the conveyance controller and scanner controller to determine whether additional modification to the dose instructions and conveyance instructions, and additional scanning, is necessary (Step 216). In one embodiment, the conveyance controller and the scanner controller are a real-time conveyance controller and a real-time scanner controller, and the scan data can be analyzed in real time and the updated dose and conveyance instructions generated in real time.

Once the scanner controller and the conveyance controller have determined that no further adjustments to the inspection system 100 are necessary, the data processor 130 can merge the scan data with user input, weight and size information, and object characteristic information (Step 217). Based on the merged scan data, the data processor 130 can determine a optimal image presentation parameters, including image contrast and color (Step 218). The data processor 130 can also analyze the scan data (Step 219) and the scan data can be adjusted as necessary to provide a scan image in accordance with the analyzed data, the object characteristic information, and any user input information regarding the object (Step 220). The optimal image parameters and the adjusted scan data can be merged to provide to the display device 136 an optimized scan image and notification of the detection of any object of interest or radioactive material (Step 221). The data processor 130 can archive any scan data and user-generated content on the storage device associated with the data processor 130 (Step 222).

The data processor 130 and/or user can determine whether additional modification to the dose instructions and conveyance instructions, and additional scanning, is necessary (Step 223). Using the data processor 130, the user can view, analyze, and adjust data associated with the object, the configuration of x-ray scanning system 120 and conveyance system 110, current and historic scan data, and/or any other data or parameters stored on the data processor 130. It is contemplated that both the x-ray scanning system 120 and conveyance system 110 can be configured to receive user input adjusting the x-ray scanner 122 and the conveyor 112 and that the user can define the x-ray dose or the scan speed to be applied to the target region (Step 224). It is also contemplated that the data processor 130 can adjust the conveyance instruction and the scan instruction based on a user definition of the inspection region. For example, the data processor 130 can notify the user or otherwise provide an indication that areas of the inspection region did not exhibit sufficient resolution because poor x-ray beam penetration and can identify such regions on a visual display. The user can then re-define the inspection region to the portion of the object with poor scan information and the data processor 130 can adjust the conveyance instruction and the scan instruction accordingly (Step 224). Once the conveyance instruction and scan instruction have been adjusted based on user input and based on analysis by the data processor 130, the object can be rescanned and new scan data can be acquired (Step 225).

Figure 4:
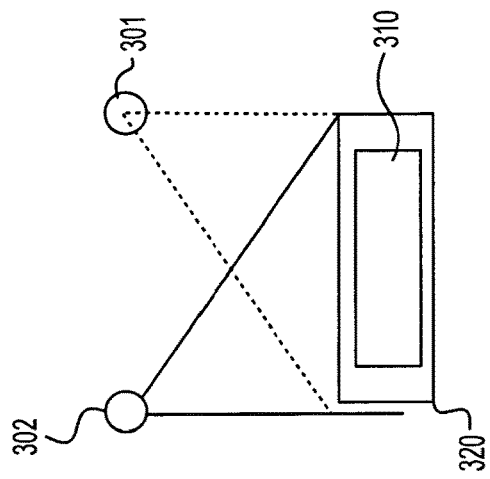
Figure 3B:
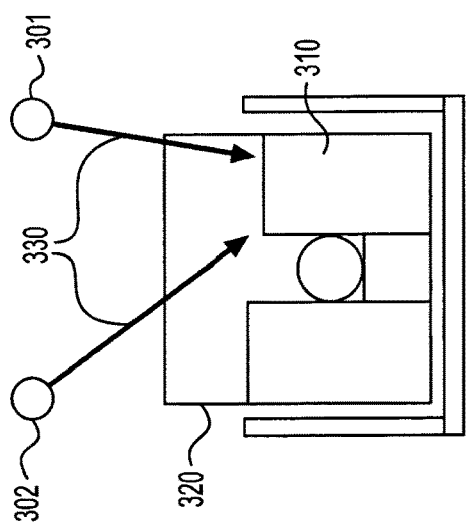
Figure 3A:
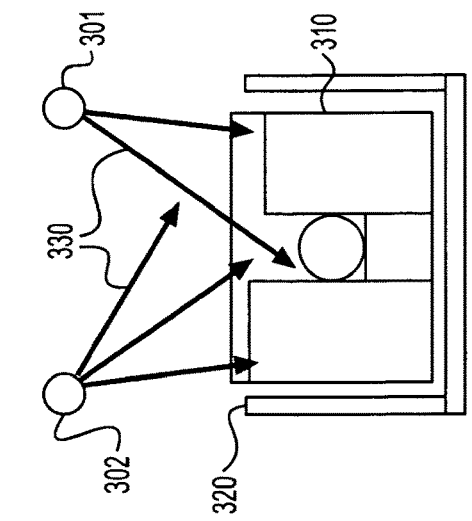

FIGS. 3-5 illustrate a dual view radioscopic inspection system consistent with an embodiment of the present disclosure. By way of example only, FIGS. 3-5 illustrate the combined use of a first x-ray scanner 301 and a second x-ray scanner 302. The first x-ray scanner 301 and the second x-ray scanner 302 can emit radiation 330 into a scanning region, through which an object 310 passes. The object 310, further, can be located within a container 320. FIG. 4 illustrates, generally, a dual view radioscopic inspection system, and FIG. 5 depicts a dual view radioscopic inspection system on a trailer 501. FIGS. 3A-5 illustrate the use of dual view x-ray scanning and material discrimination and corresponding points location to improve, for example, threat detection. For example, by coordinating the scan data from the first x-ray scanner 301 with the scan data from the second x-ray scanner 302, the location of various points corresponding to the container and/or object 301 can be identified. For instance, the dimensions of the container and/or object can be determined, e.g., the thickness of the object. Determining the corresponding points, e.g., a location of points associated with the object, can assist in the material discrimination analysis of the object 310 and/or be used to improve imaging, used as the basis for further scanning, and so on. For example, the presence and location of a threat material within or proximate to the object 310 can the determined. It is to be appreciated that a wide variety of material discrimination information may be obtained. It is the intention of this application to encompass such variation.

Material discrimination can be limited when the entire path length of multiple materials in the inspection region contribute to the determination. That is, contraband and threats can be effectively disguised by packaging. As configured herein, however, dual view radiography can have many benefits when coupled to a dual-energy data acquisition strategy. Consistent with the embodiments disclosed herein, a dual view system can utilize the initial scans to target suspicious areas with dual energy multiple views or computed tomography. By comparing the multiple views of the object 310 and any corresponding points locations missing depth information along with the density information can be retrieved. This can allow for better detection of offending materials.

Figure 6A:
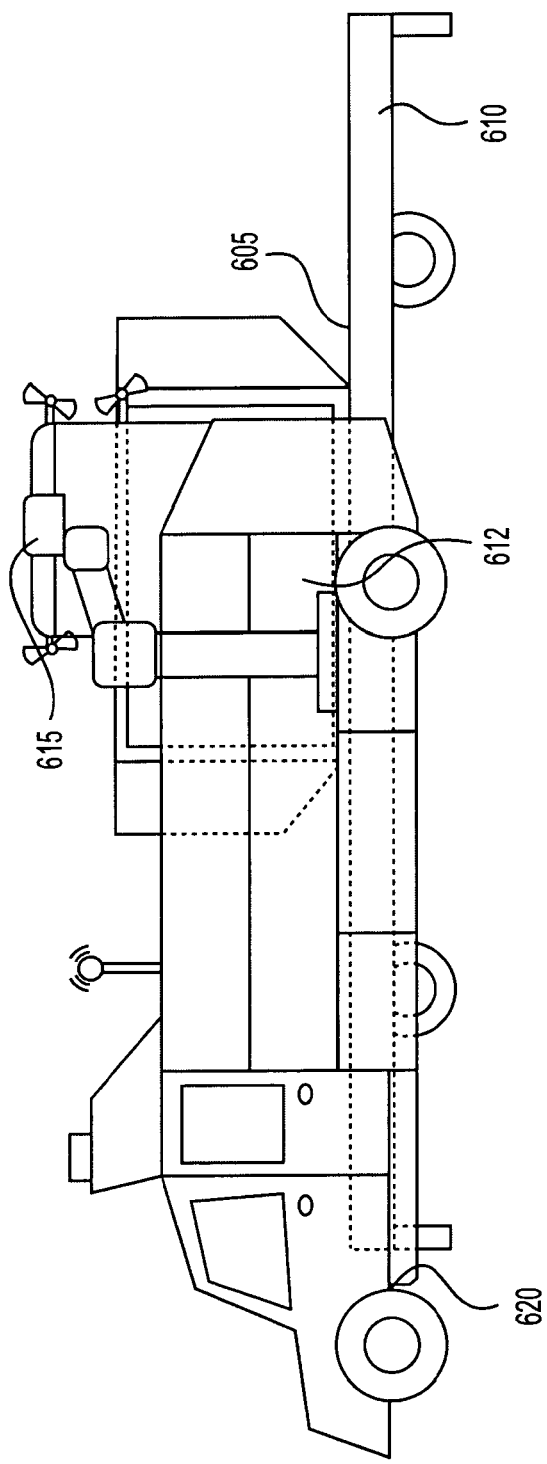
FIG. 6 depicts a trailer-based inspection system with a telescoping scanning tunnel consistent with an embodiment of the present disclosure.
Figure 6B:
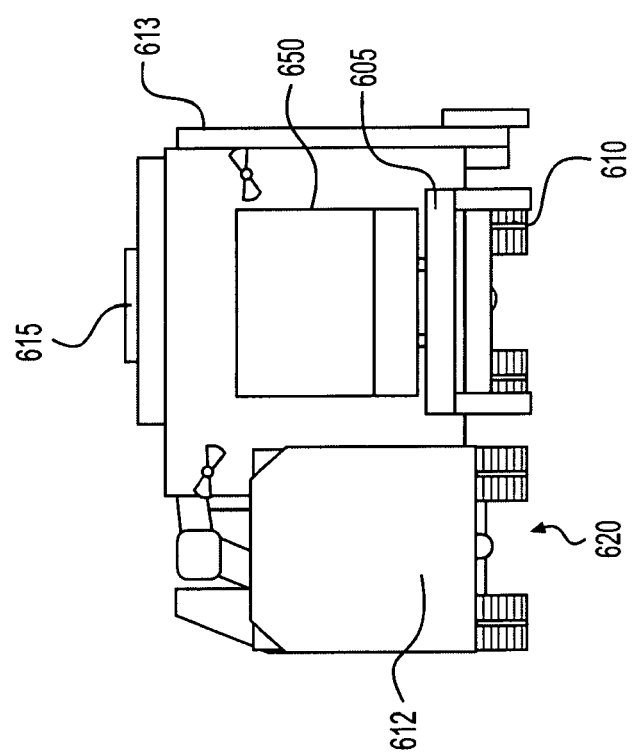
Figure 6C:
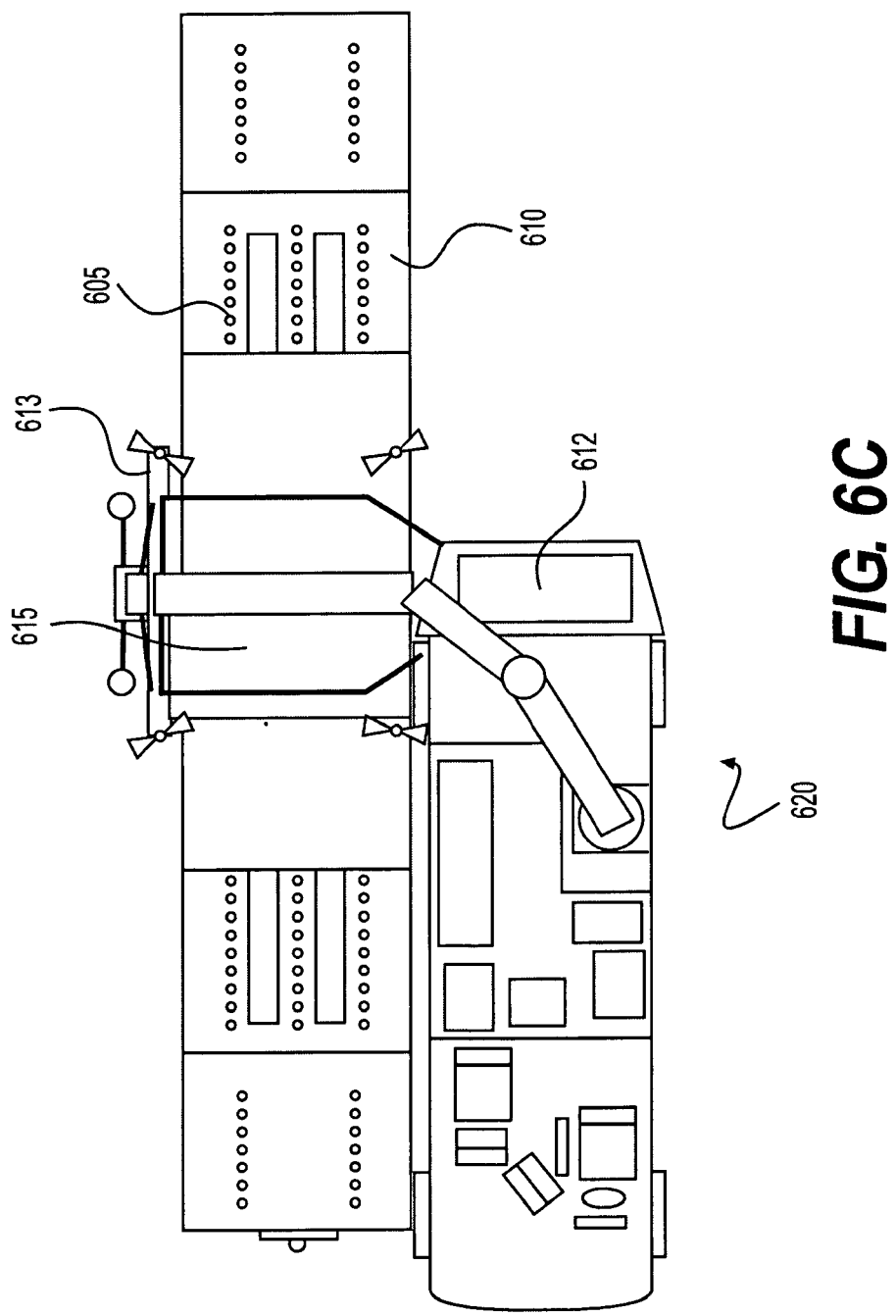

FIGS. 6A-6C depict various views of a trailer-based inspection system with a telescoping scanning tunnel consistent with an embodiment of the present disclosure. In particular, a hybrid system is shown, which integrates a mobile scanner 620 with a trailer-based conveyor 610. (In FIG. 6A, for convenience, the mobile scanner 620 is depicted as transparent.) The mobile scanner 620 is depicted alongside the trailer-based conveyor 610. A side scanner 612 (which can be a low-energy scanner) and a top scanner 615 (which can be a high energy scanner) are also depicted. A conveyor 610 includes a conveyor bed 605. Also depicted, opposite the side scanner 612, is a side detector 613.

Figure 7:
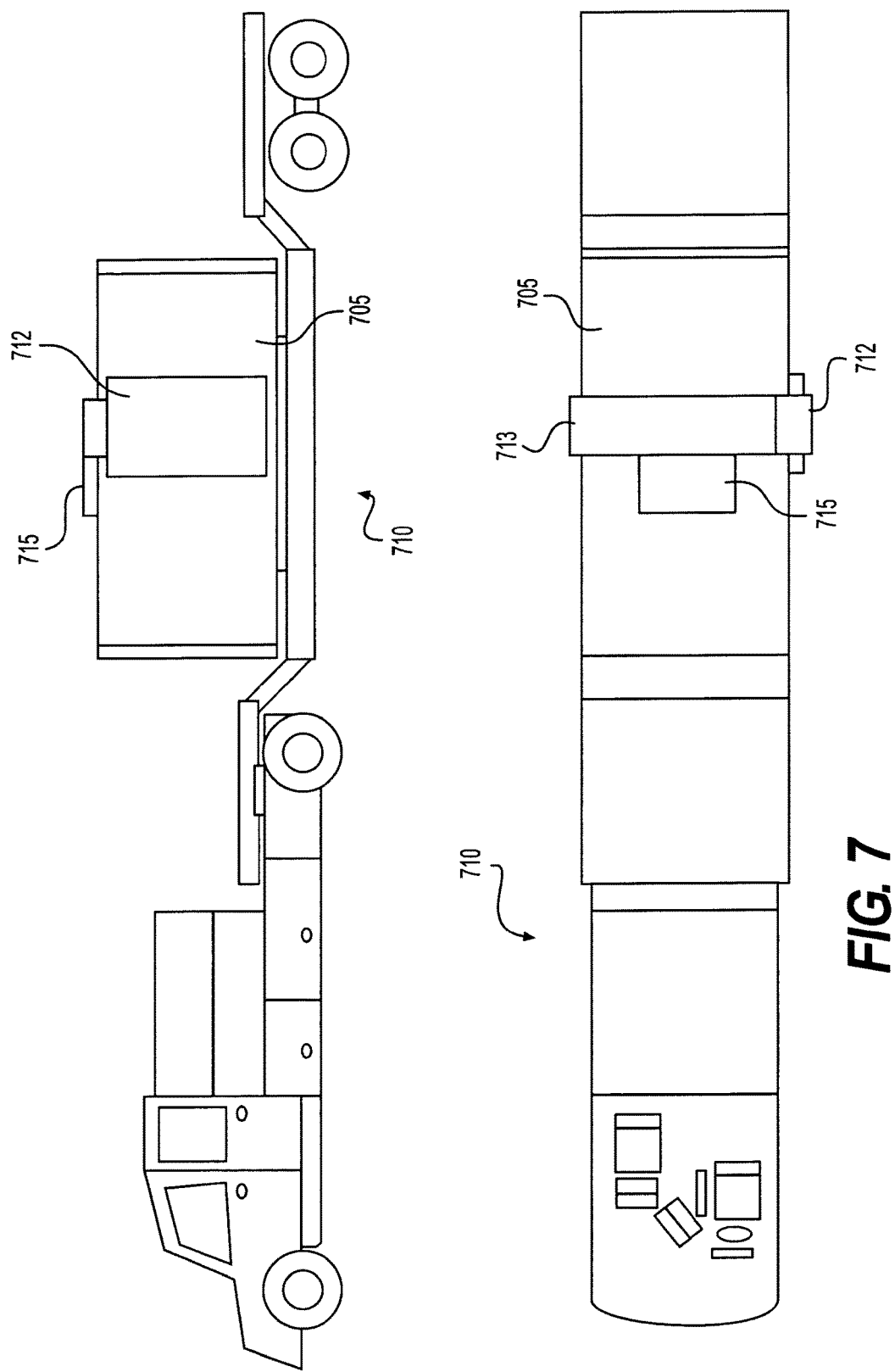
FIGS. 7-23 depict views of another trailer-based inspection system consistent with an embodiment of the present disclosure.
Figure 8:
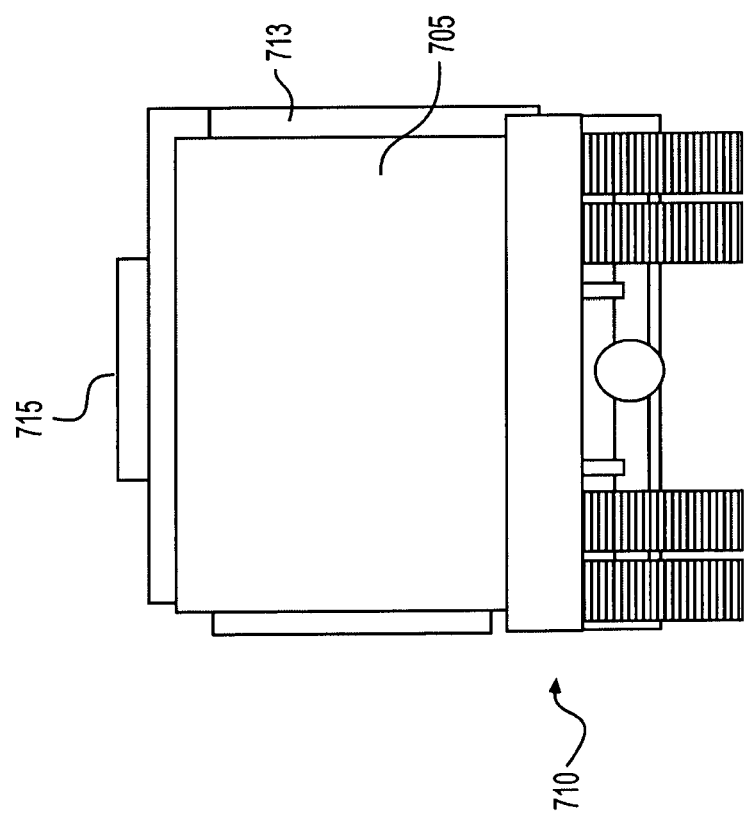

FIGS. 7-23 depict views of a trailer-based inspection system 710 consistent with an embodiment of the present disclosure. FIGS. 7 and 8 depict the trailer-based inspection system 710 configured for transportation. The position of a side scanner 712 (which can be a low energy scanner) and a top scanner 715 (which can be a high energy scanner) are shown. In addition the position of a side detector 713 is shown, as well as a combined conveyance and scanning system 705.

Figure 9:
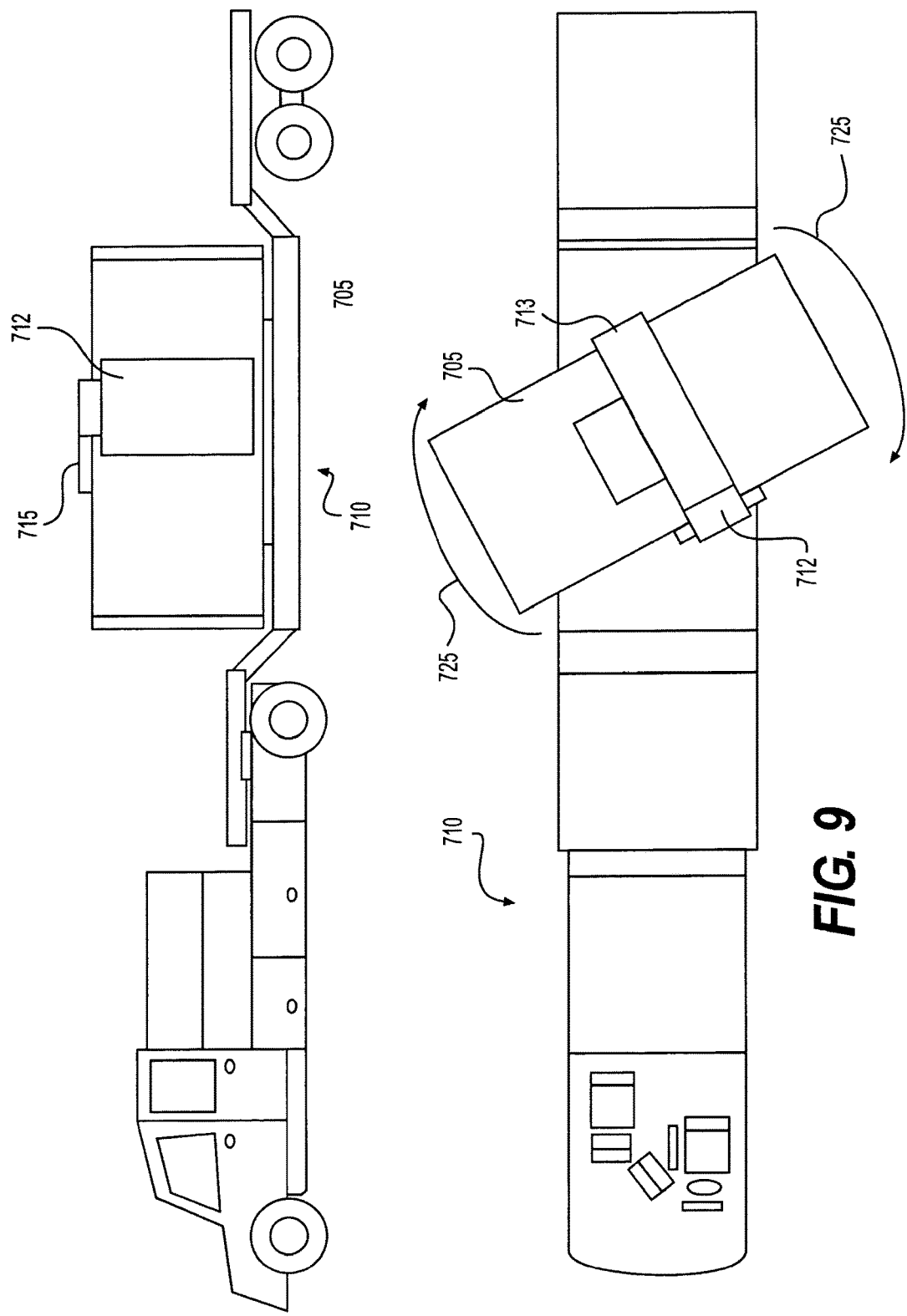
Figure 10:
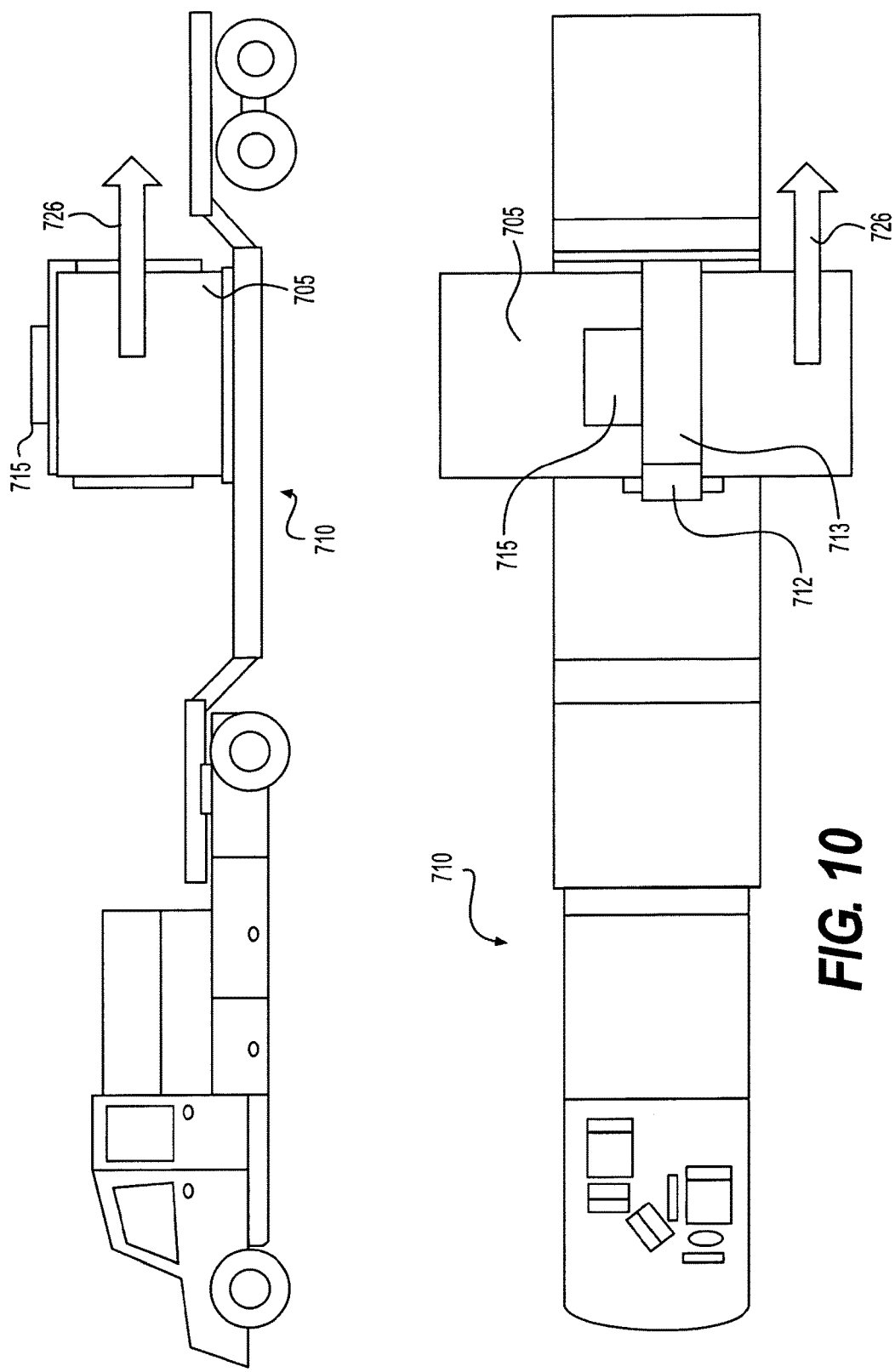
Figure 11:
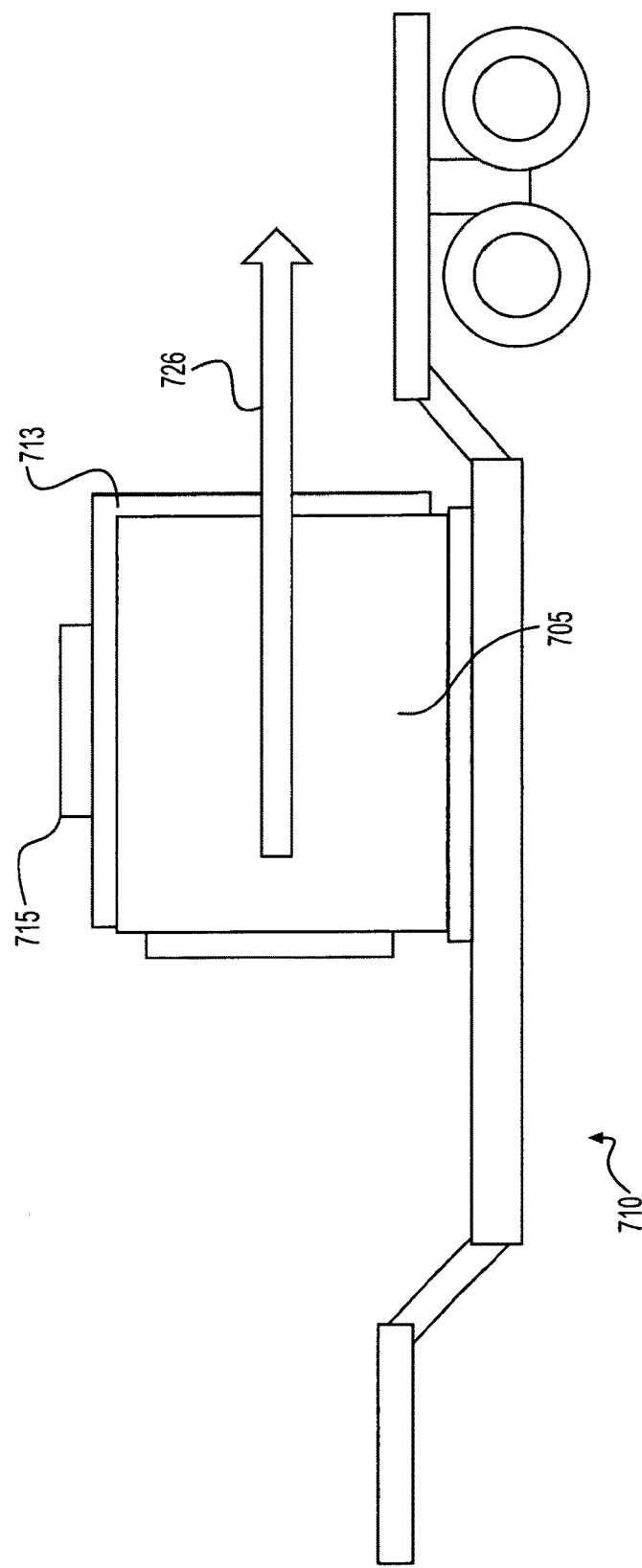
Figure 12:
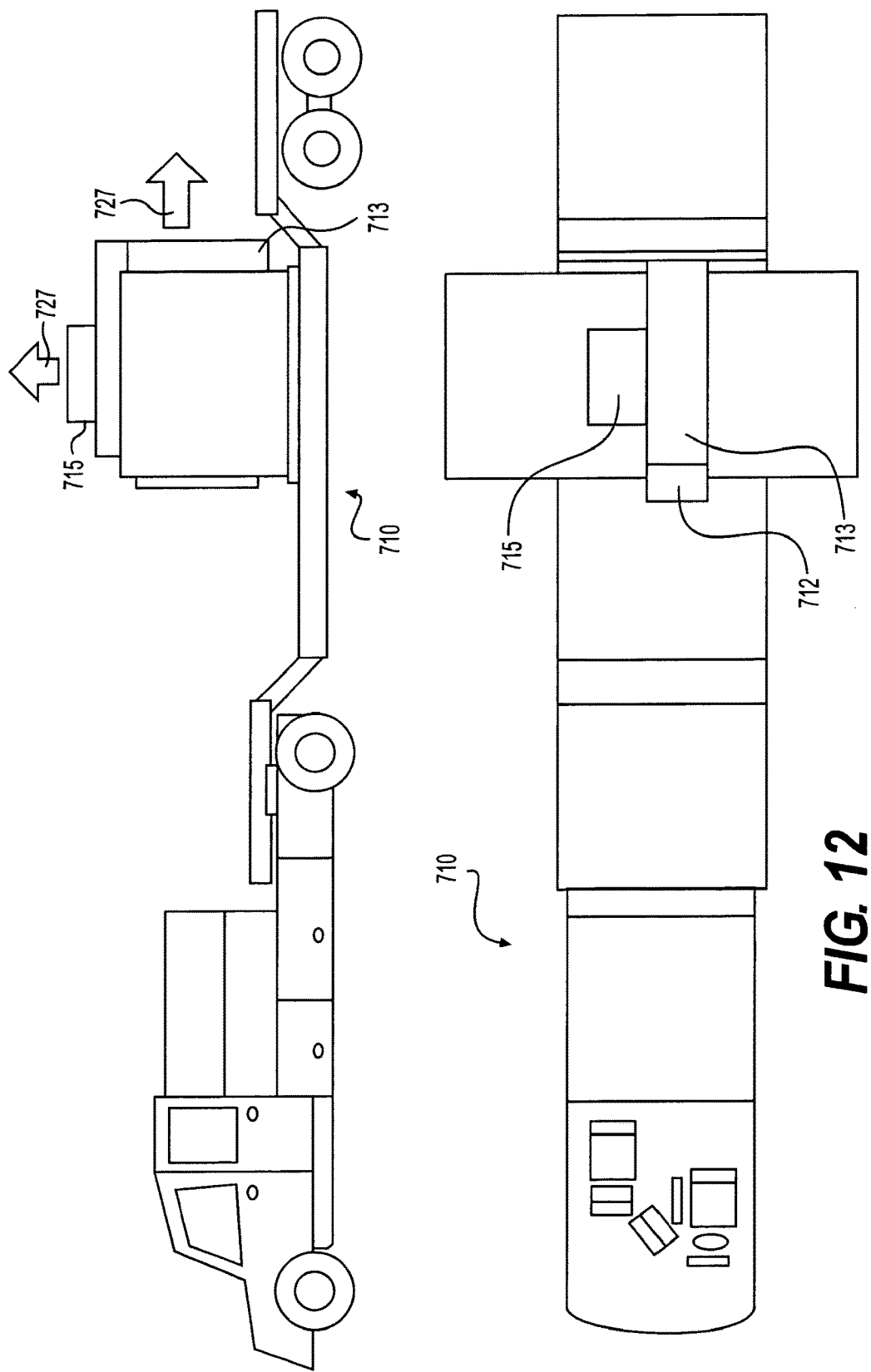
Figure 13:
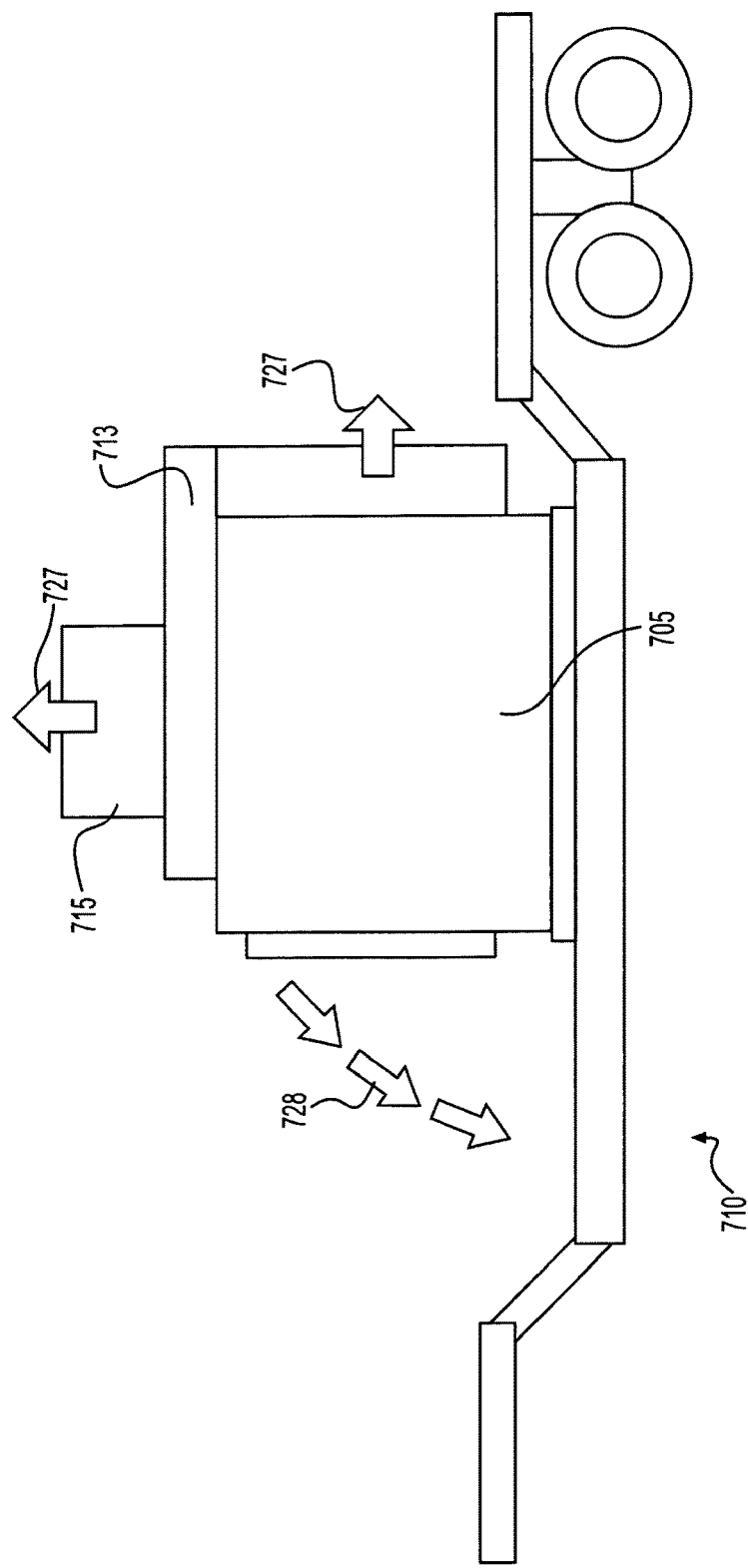
Figure 14:
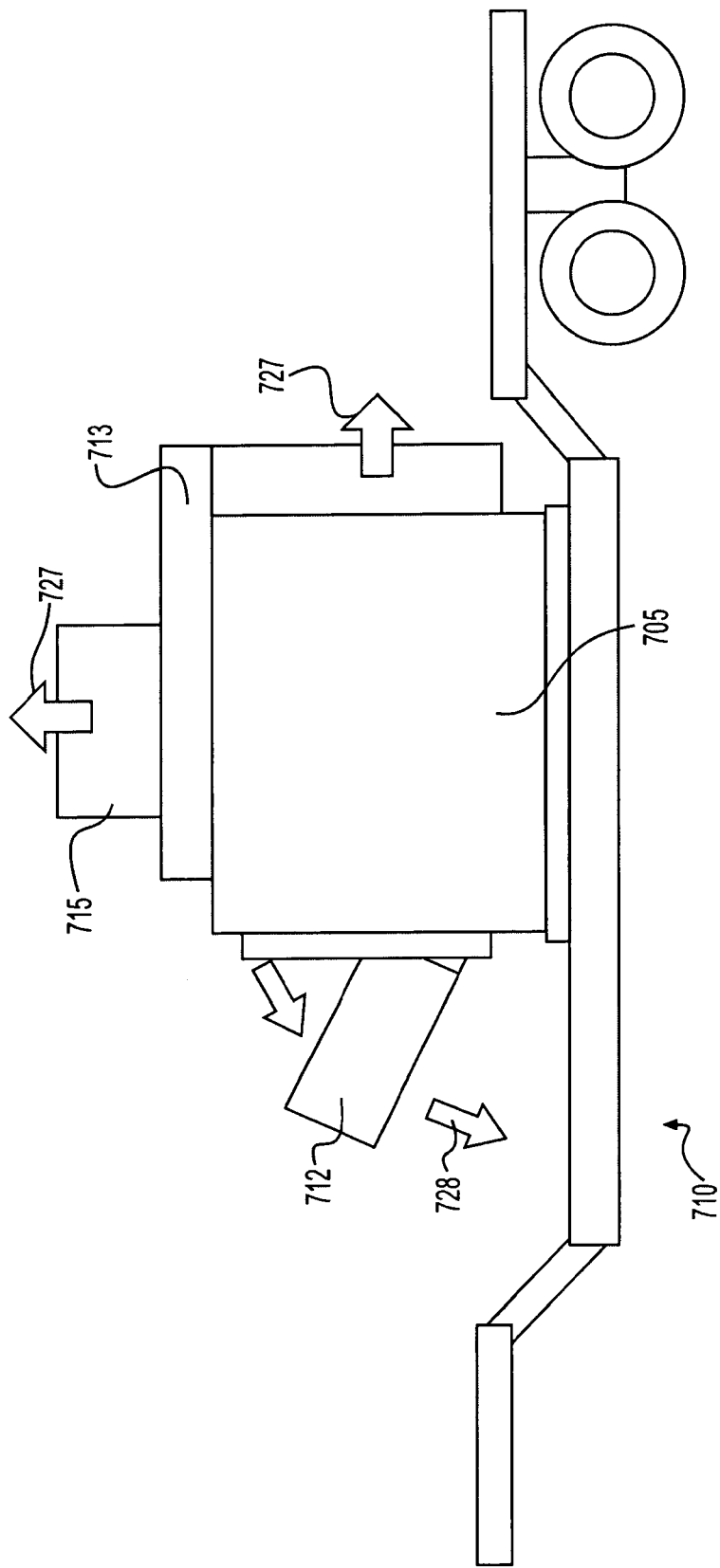
Figure 15:
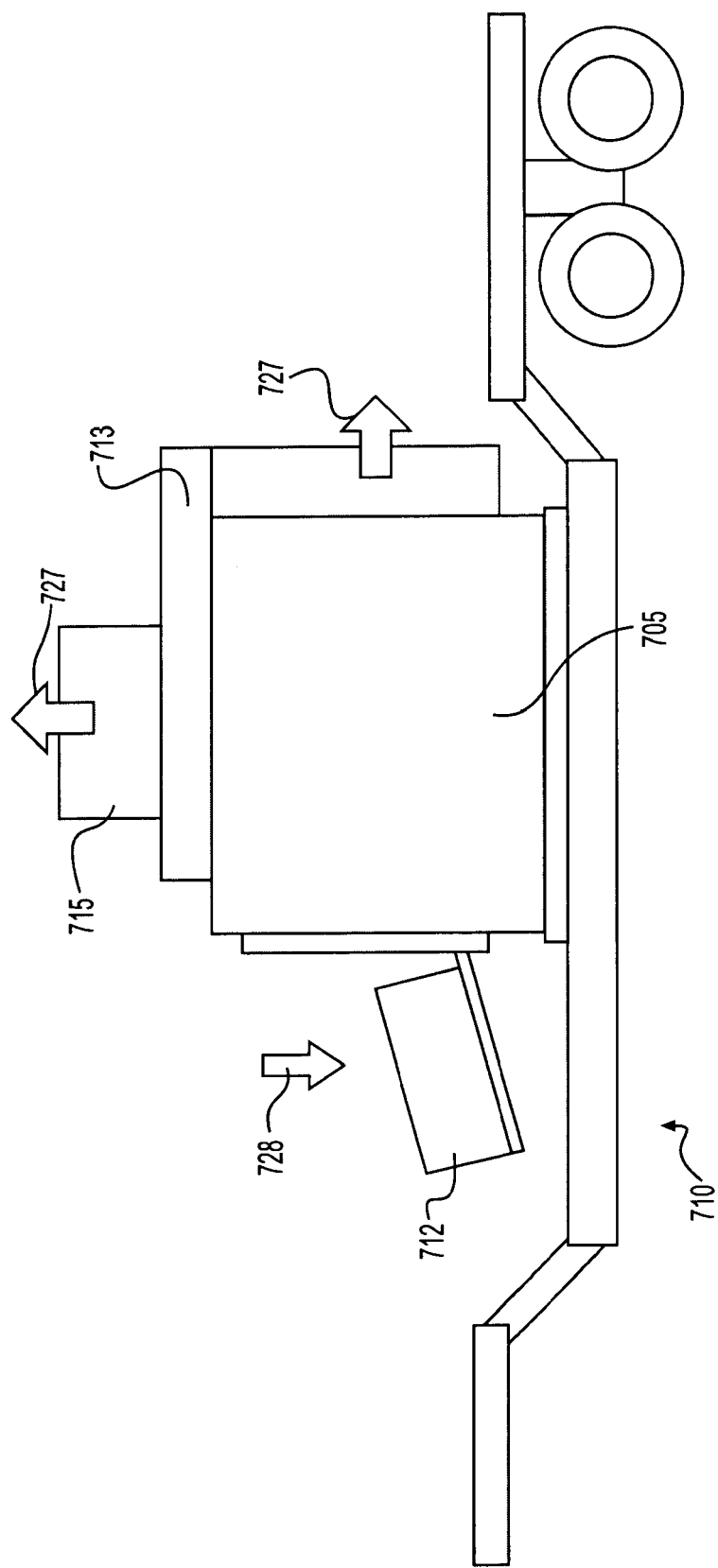
Figure 16:
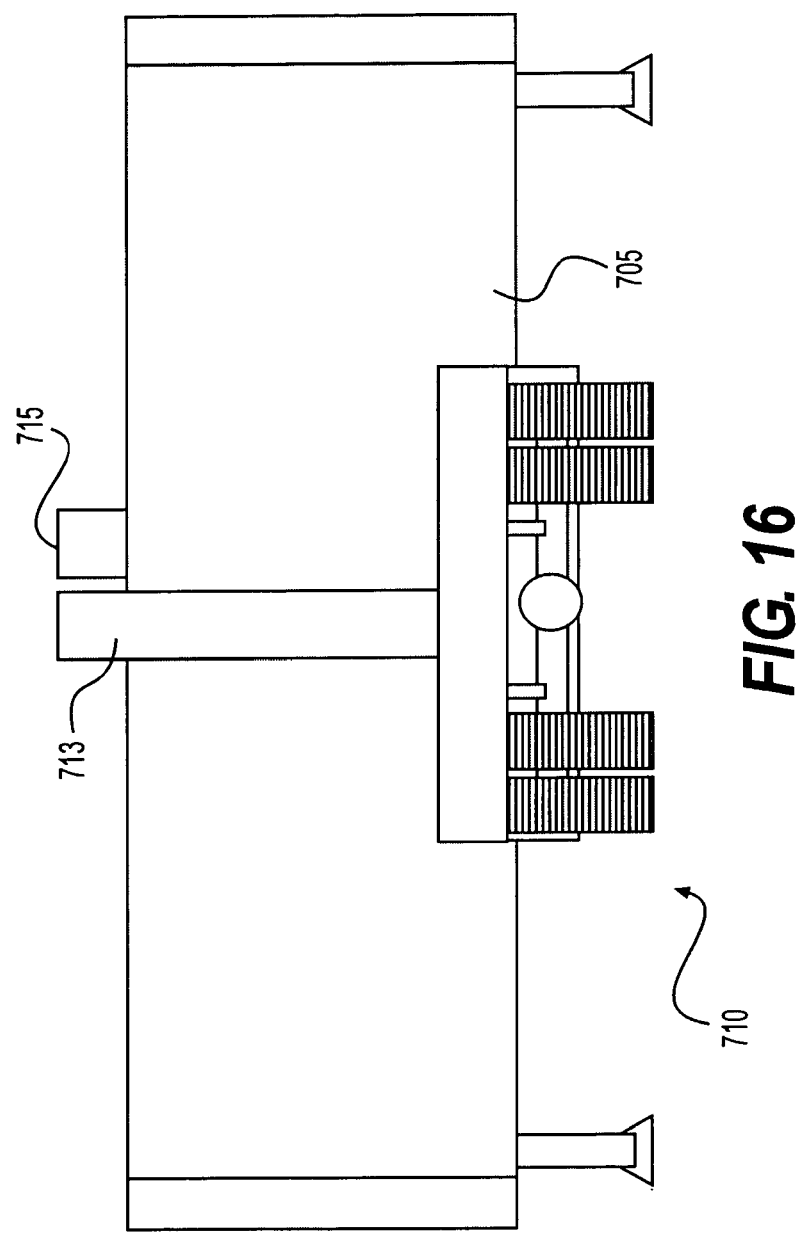
Figure 17:
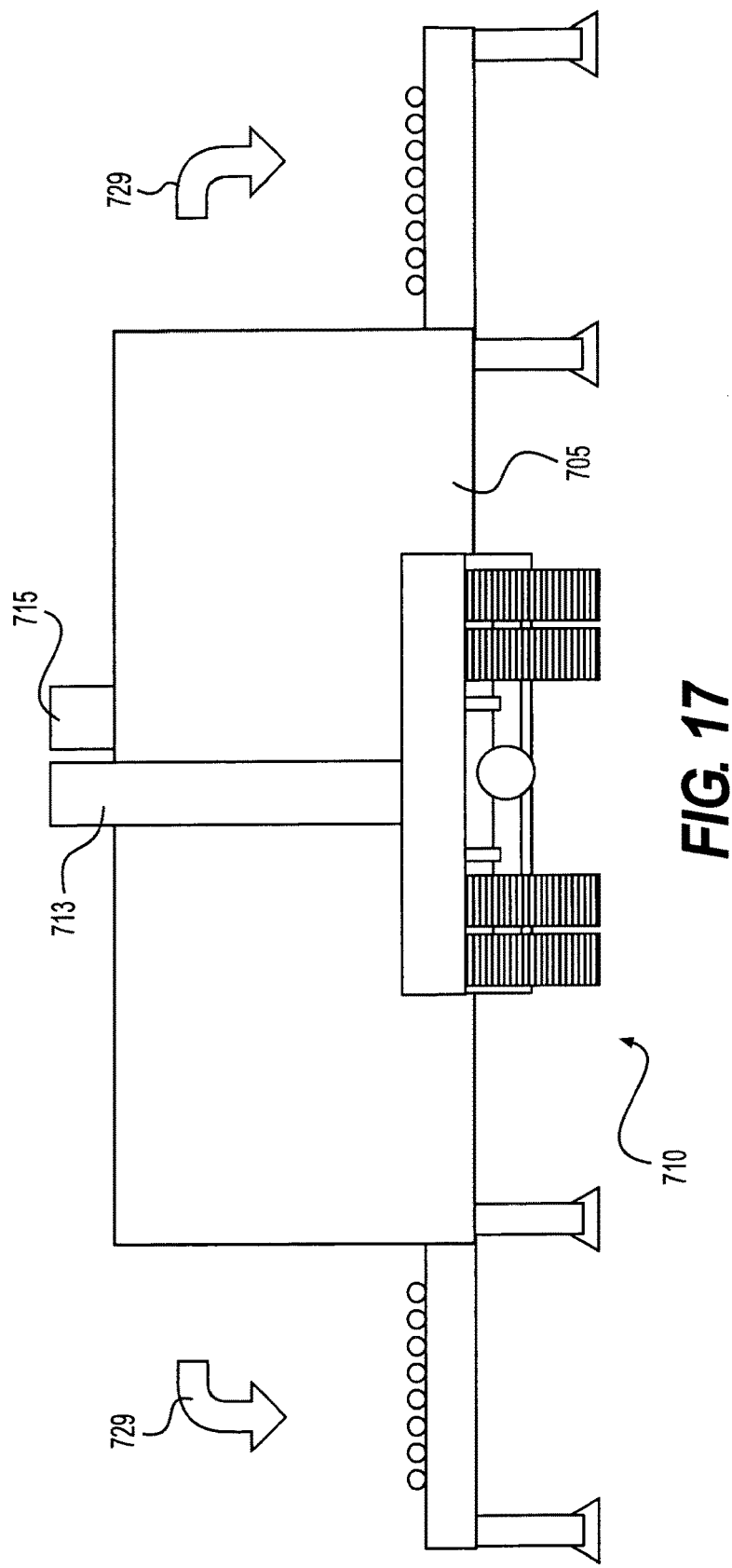
Figure 18:
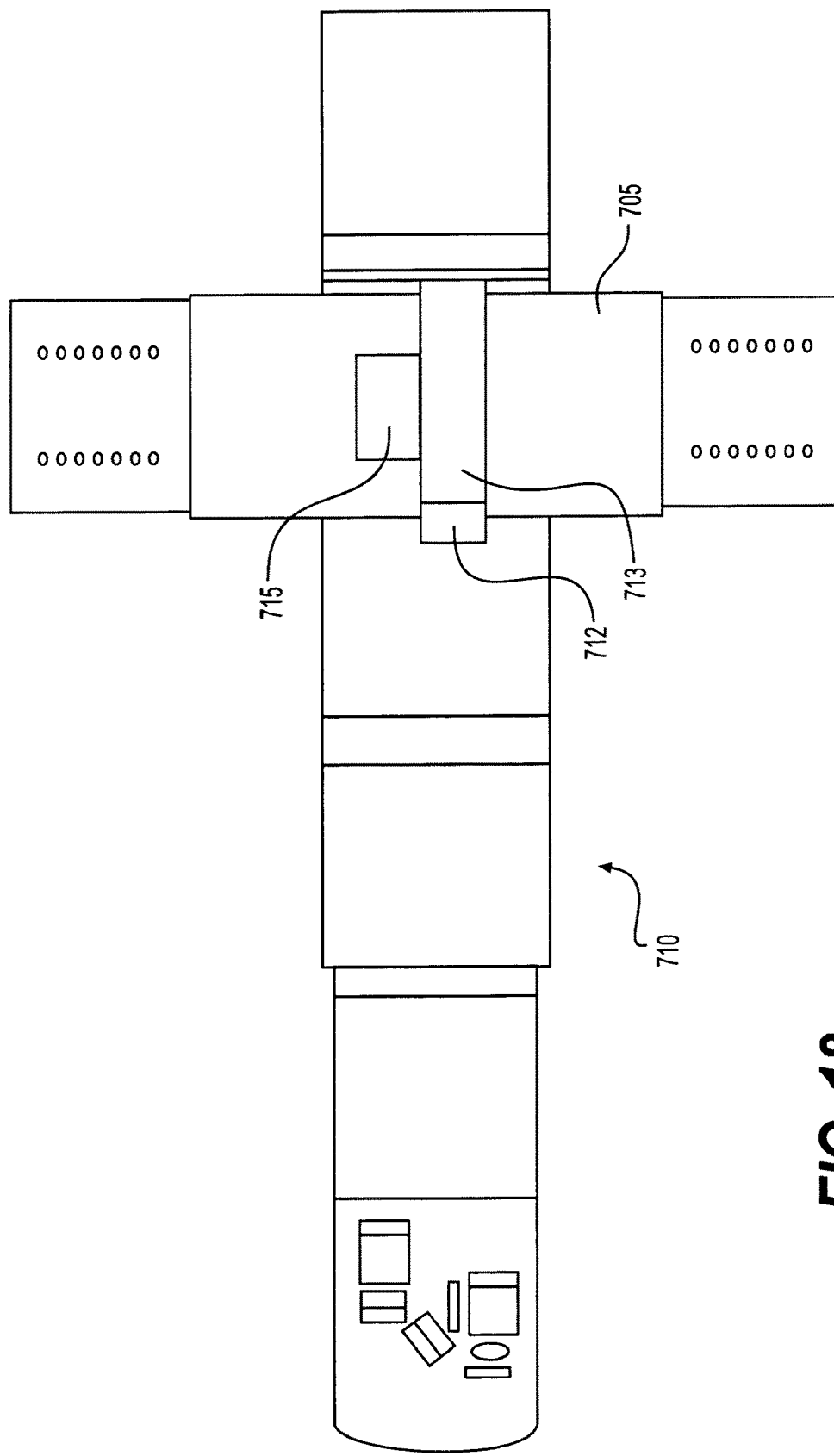
Figure 19:
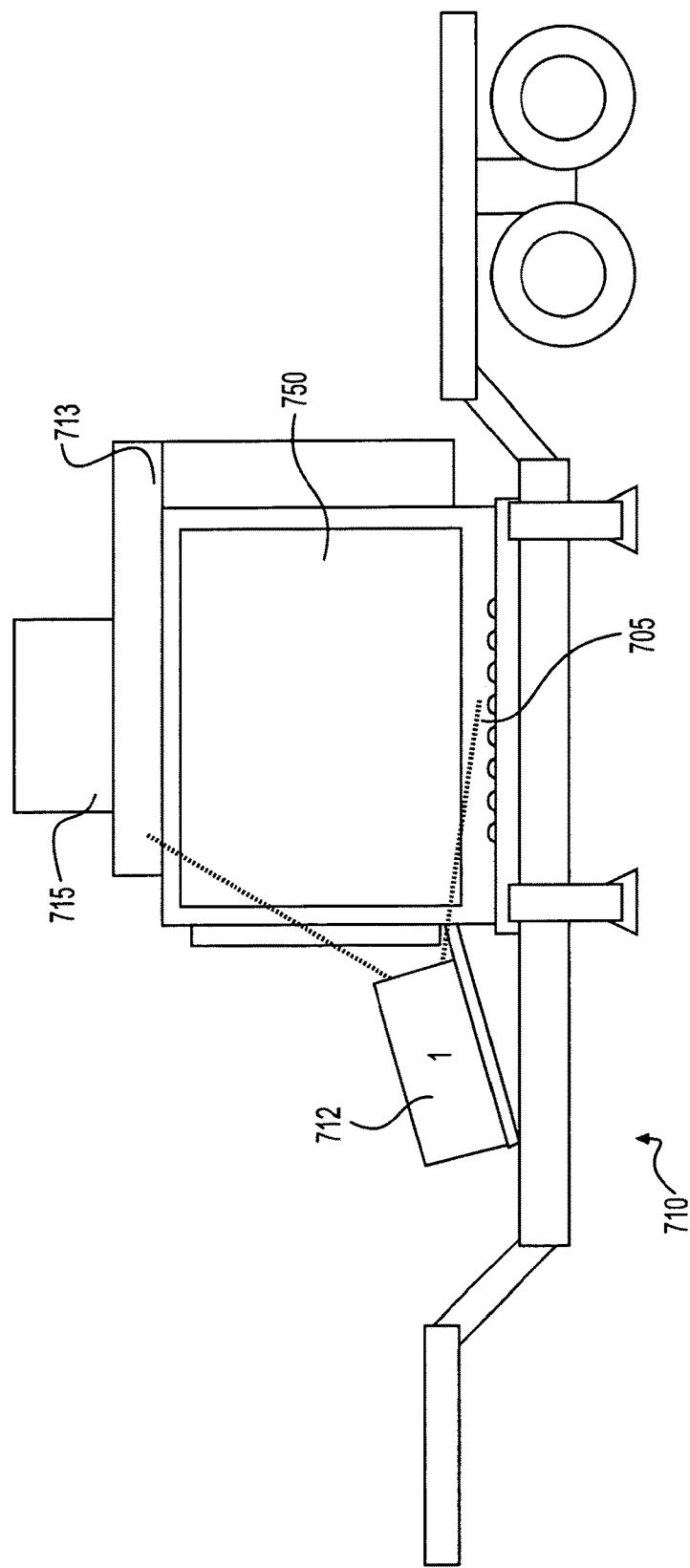
Figure 20:
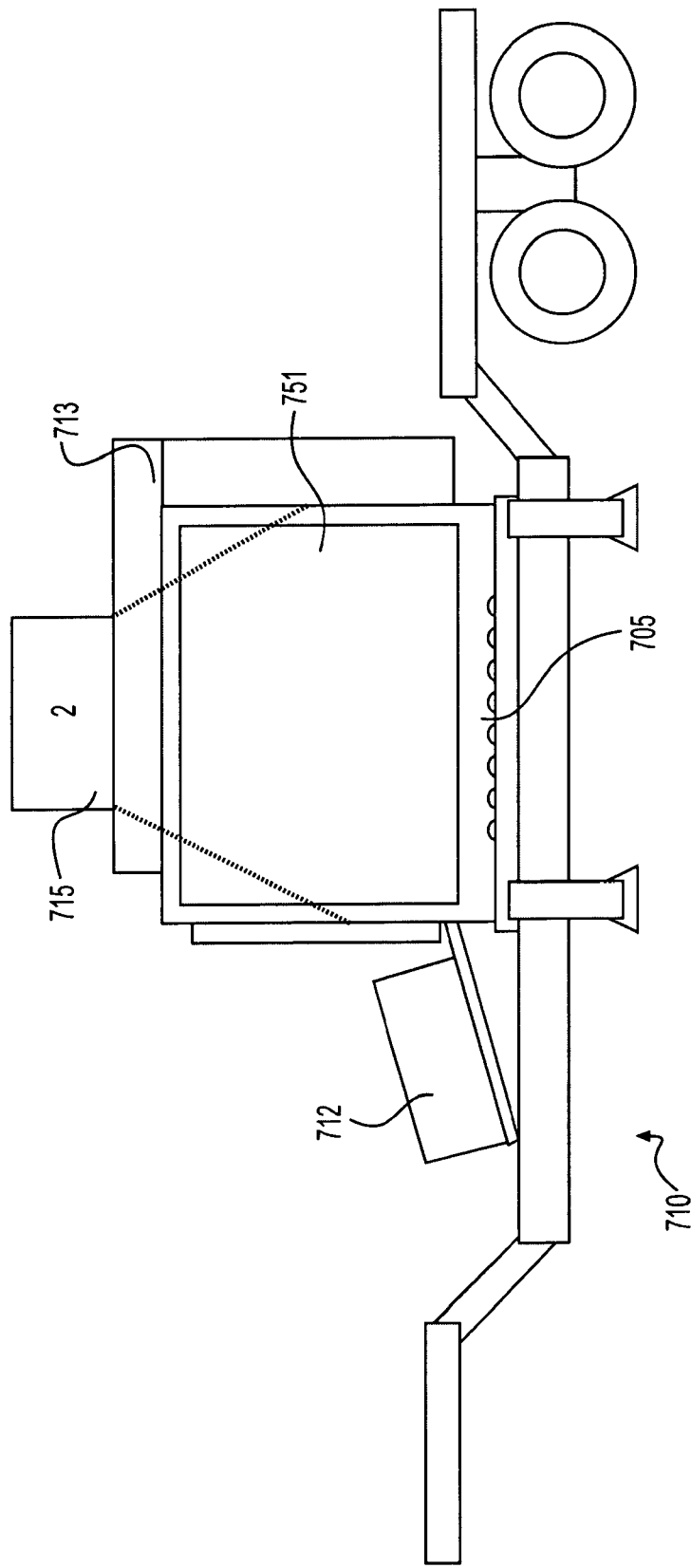
Figure 21:
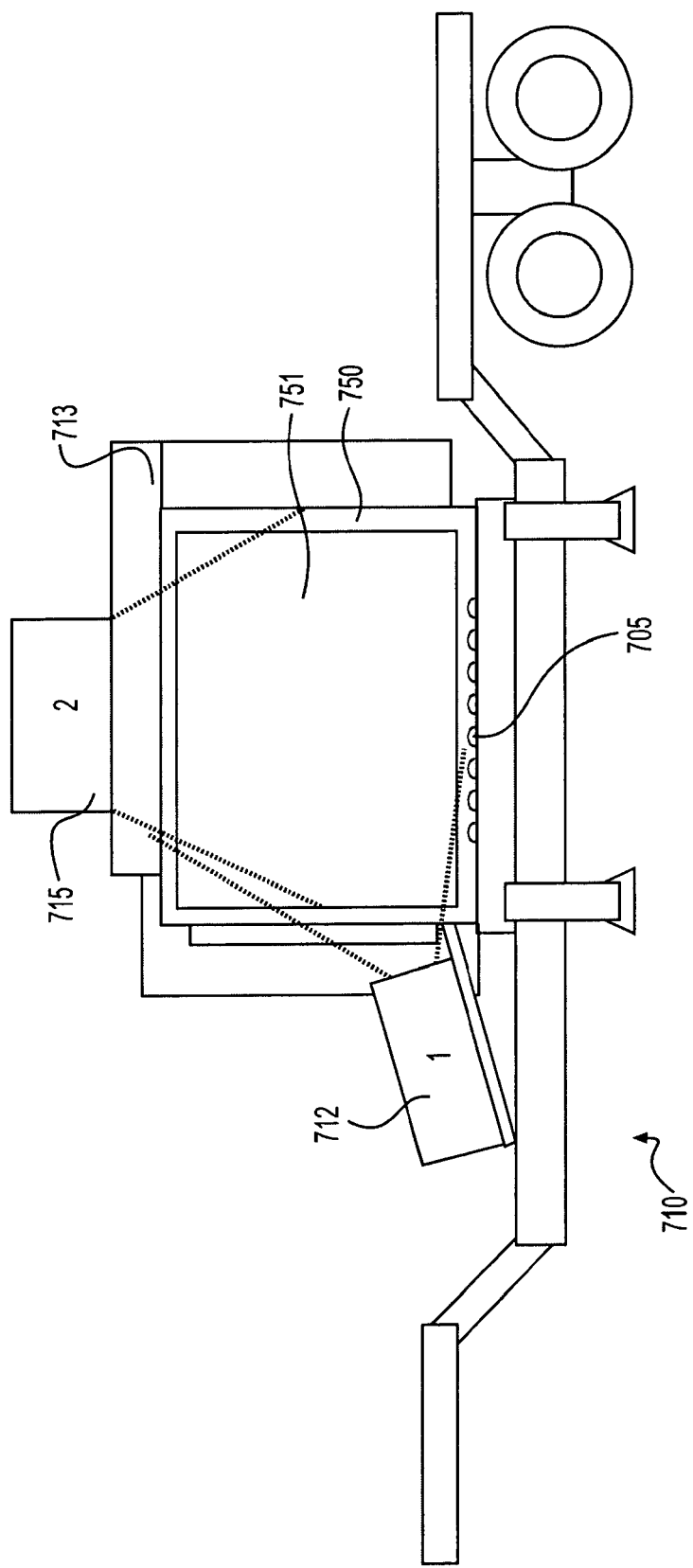
Figure 22:
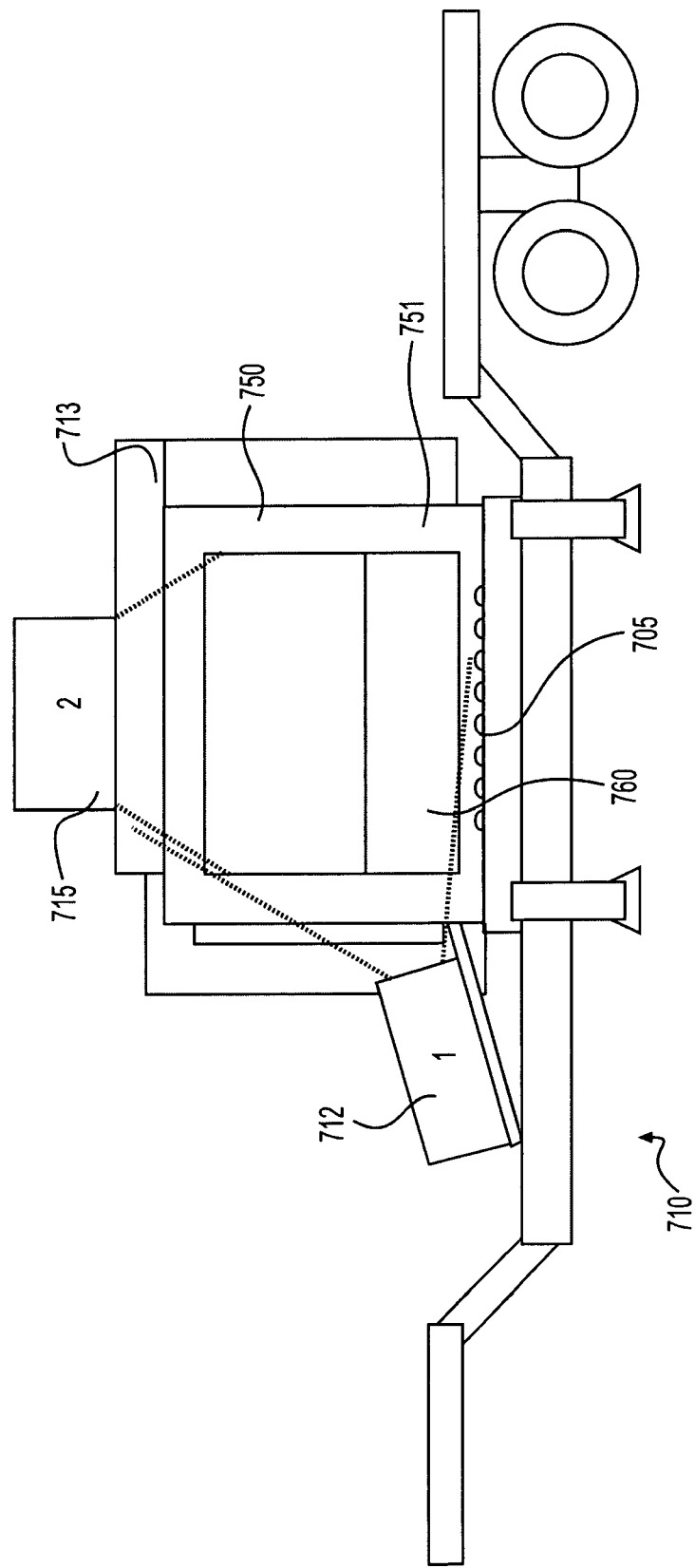

FIGS. 9-11 illustrate how the trailer-based inspection system 710 can be initially manipulated to be configured for scanning from its transportation configuration. The combined conveyance and scanning system 705 can be rotated, as depicted by arrows 725, and translated, as depicted by arrows 726, so as to be reoriented for a scanning configuration. FIG. 12 illustrates how the side detector 713 and the top scanner 715 can be translated (as by arrows 727) so as to be in a scanning configuration. FIGS. 13-15 illustrate how the side scanner 712 can be reoriented from its transportation configuration (as by arrows 728) so that it is oriented to direct radiation back into a chamber 705. FIGS. 16 and 17 illustrate how a conveyance system can be unpacked from transportation mode to scanning mode (as illustrated by arrows 729.) In addition, the relative orientation of the side detector 713 and the top scanner 715 is shown. FIG. 18 is a top view of the configuration depicted in FIG. 17.

Figure 23:
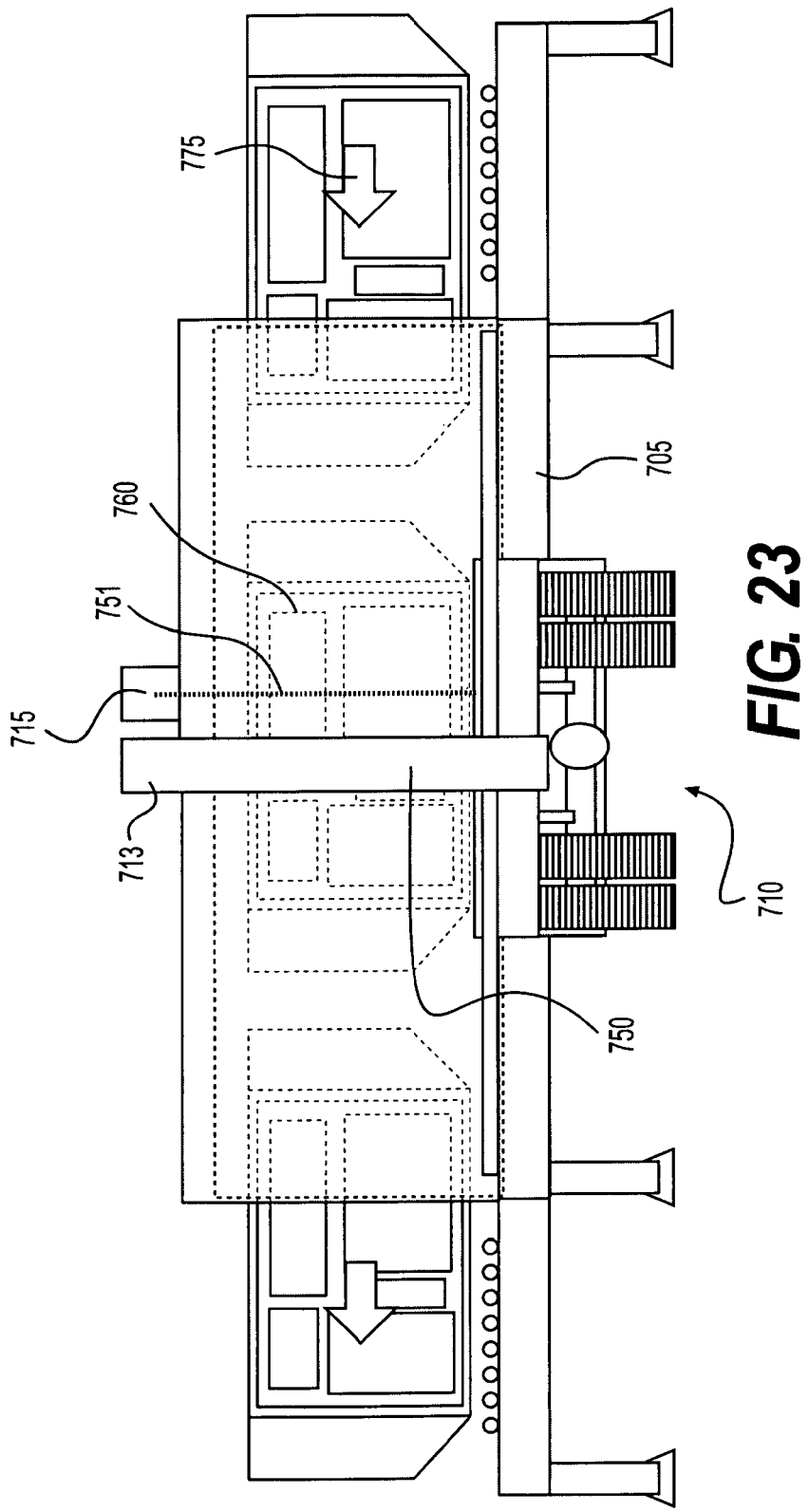

FIGS. 19-22 depict the side scanner 712 and the top scanner 715 supplying radiation to scanning regions 750 and 751, respectively. In particular, FIG. 22 also depicts a container 760 moving through the scanning region 750 and the scanning region 751. FIG. 23 is an alternate view of FIG. 22 as depicted from the rear of the trailer-based inspection system 710. Note that the scanning region 750 can be associated with the side scanner 712 and the scanning region 751 is associated with the top scanner 715.

Figure 24:
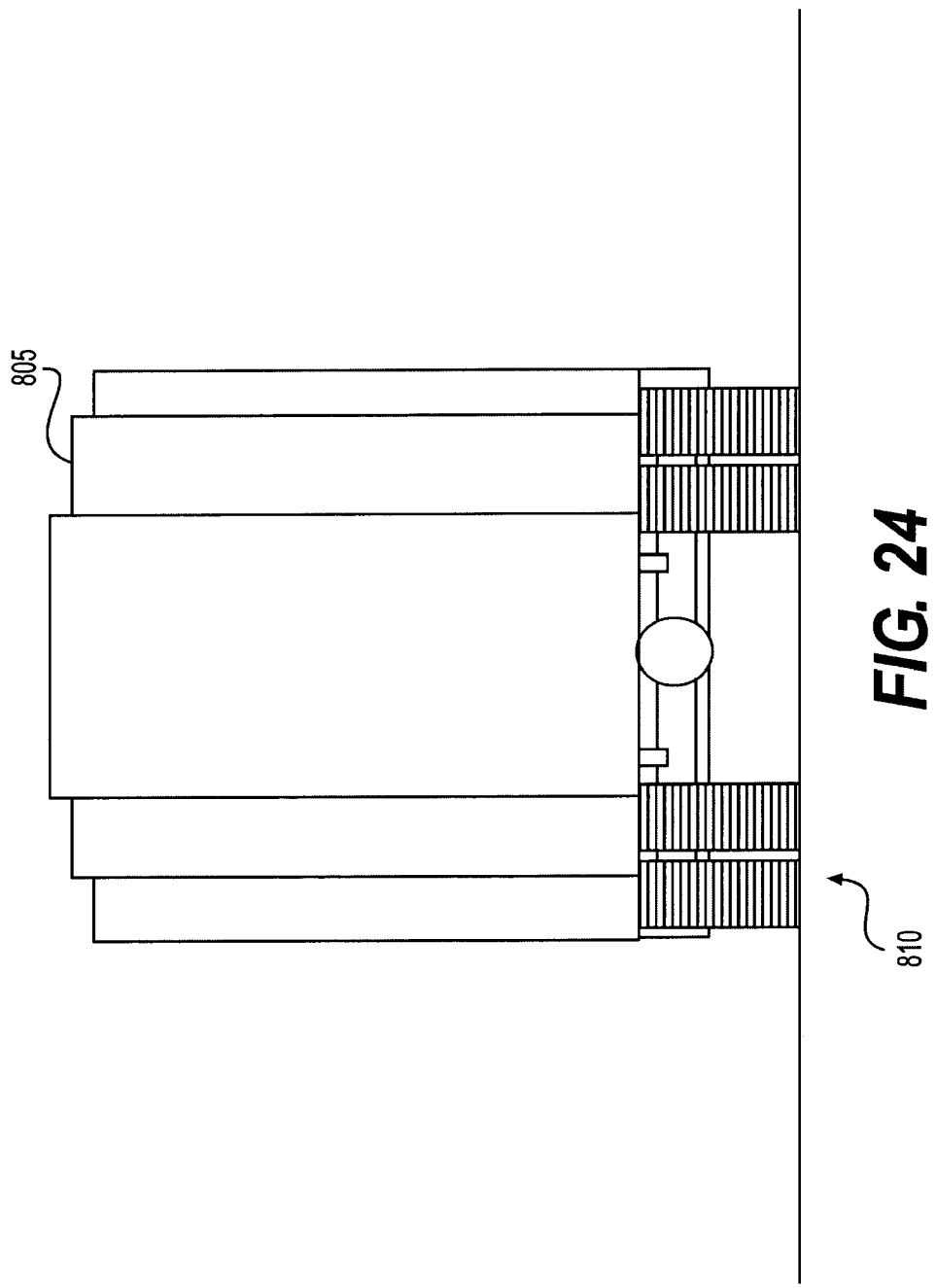
FIGS. 24-27 depict views of another trailer-based inspection system consistent with an embodiment of the present disclosure.
Figure 25:
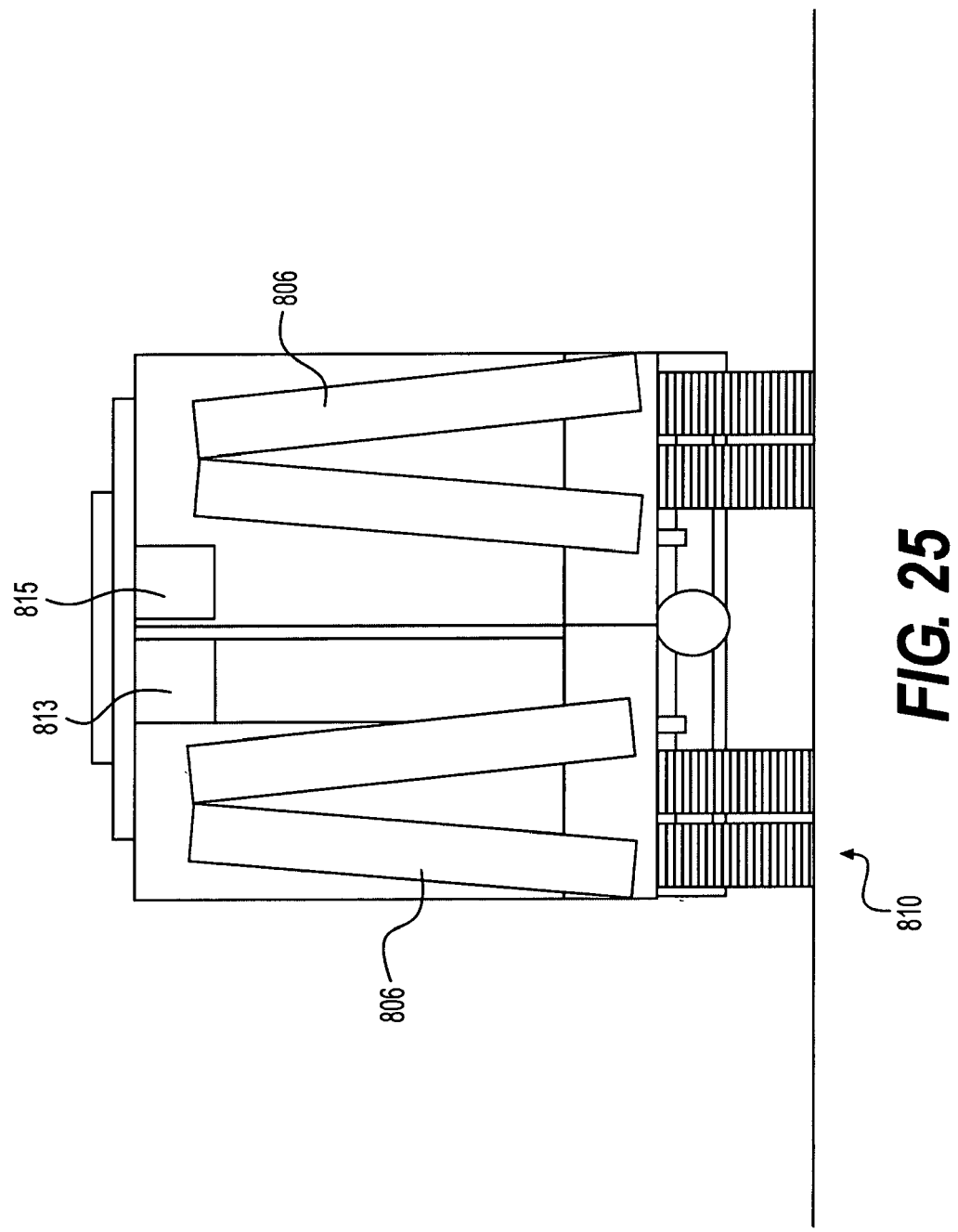

FIGS. 24-27 depict views of a trailer-based inspection system 810 consistent with an embodiment of the present disclosure. In particular, FIG. 24 is a view from the rear of the trailer-based inspection system 810, and FIG. 25 is an alternate view with walls 805 of the trailer-based inspection system 810 depicted as transparent so that a conveyance system 806, a top scanner 815, and a side detector 813 can be more conveniently viewed.

Figure 26:
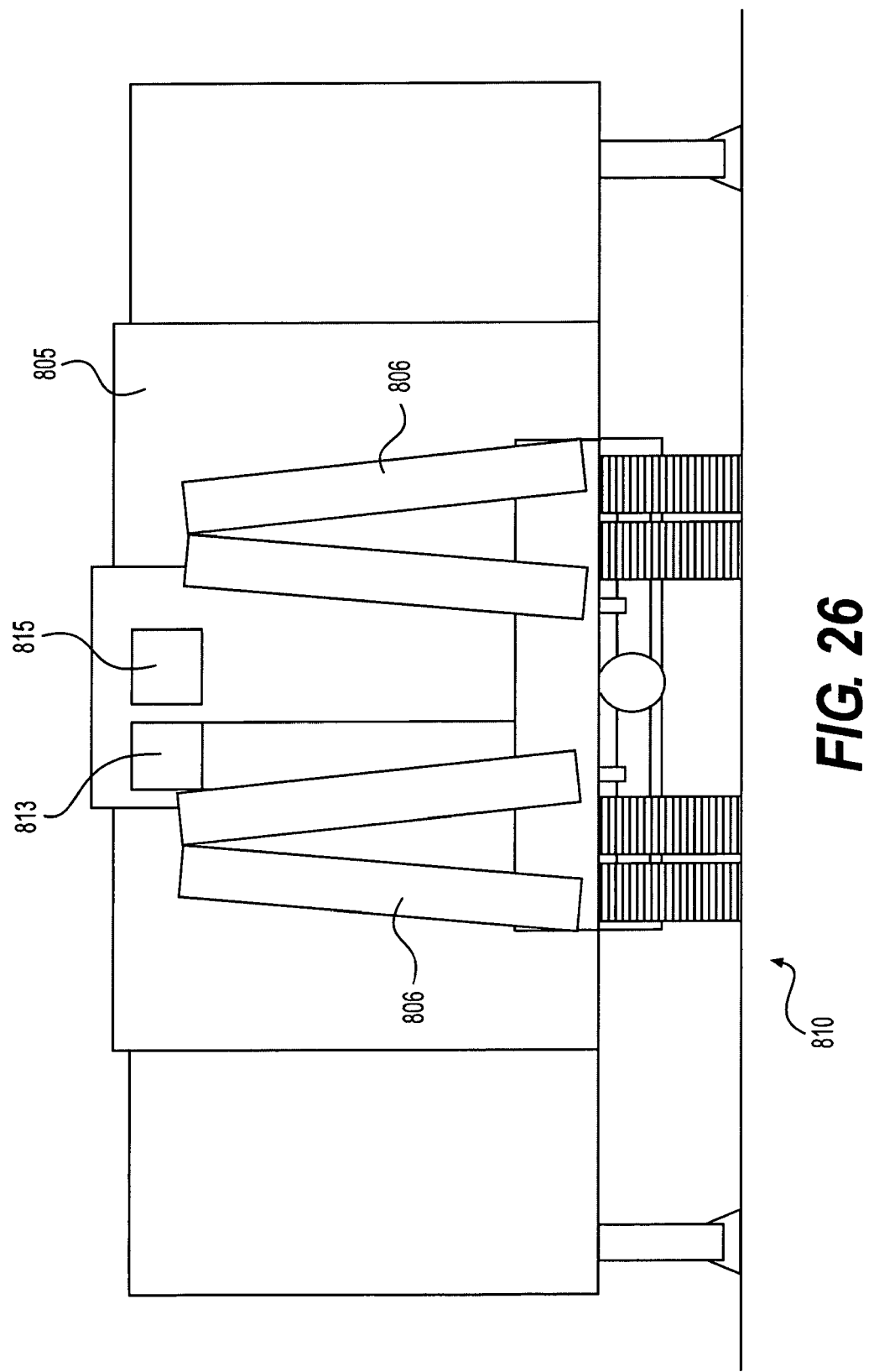

FIG. 26 depicts how the trailer-based inspection system 810 can be manipulated from a transportation configuration (depicted in FIGS. 24 and 25) to a scanning configuration. Again, the conveyance system 806, the top scanner 815, and the side detector 813 are shown through the walls 805—which are depicted as transparent solely for convenience.

Figure 27:
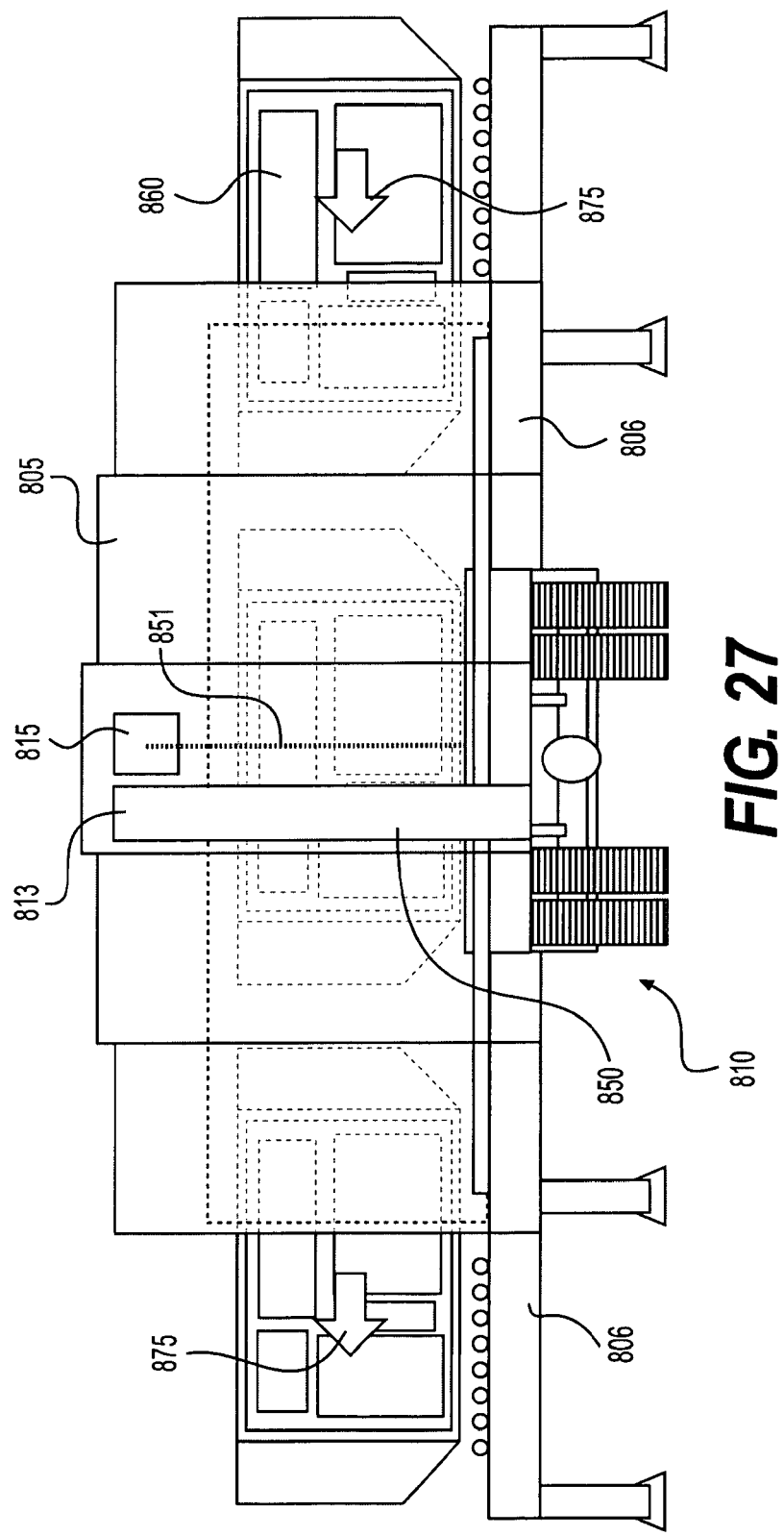

FIG. 27 depicts the conveyance system 806 unpacked into scanning configuration, and also depicted are containers 860 for scanning. Again, a scanning region 850 is associated with a side scanner (not shown) and a scanning region 851 is associated with the top scanner 815.

Figure 28:
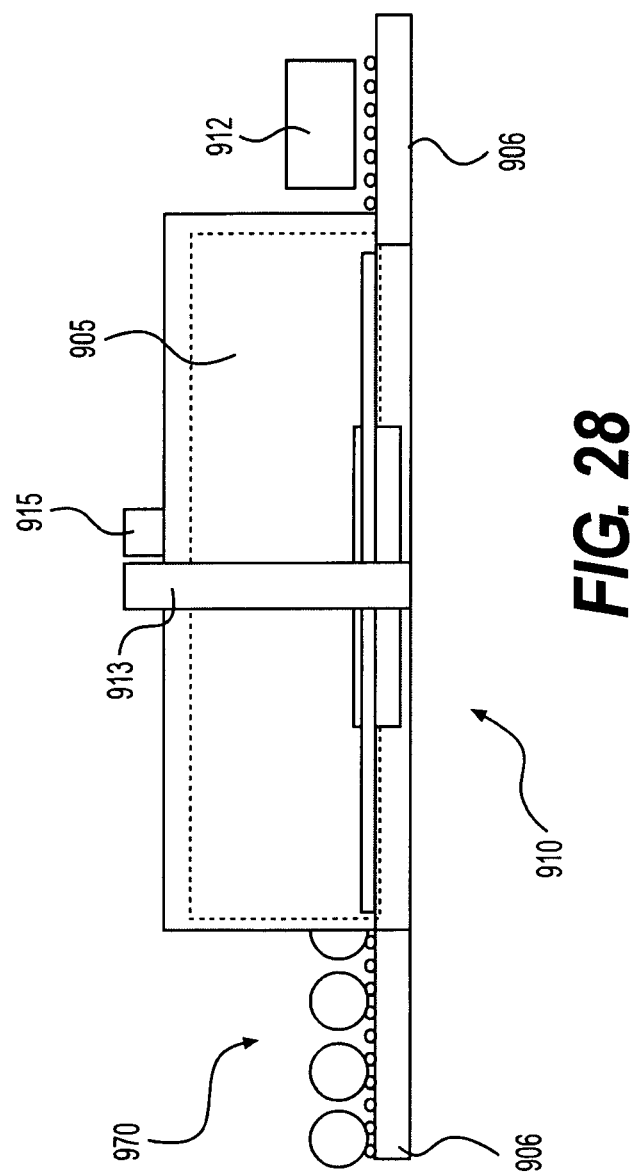
FIGS. 28-35 depict views of another trailer-based inspection system consistent with an embodiment of the present disclosure.
Figure 29:
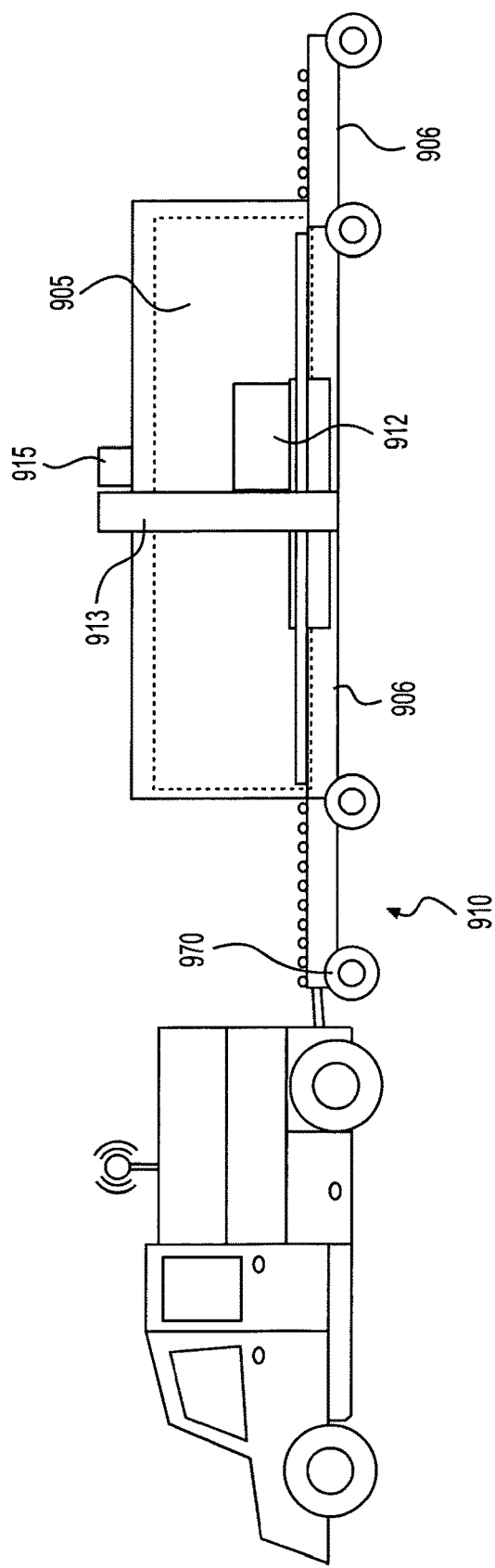
Figure 30:
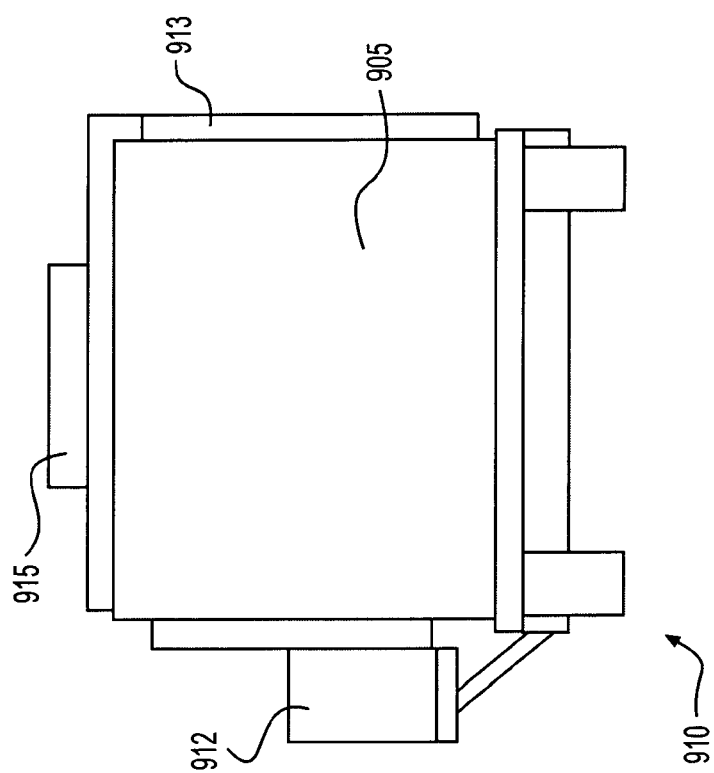
Figure 31:
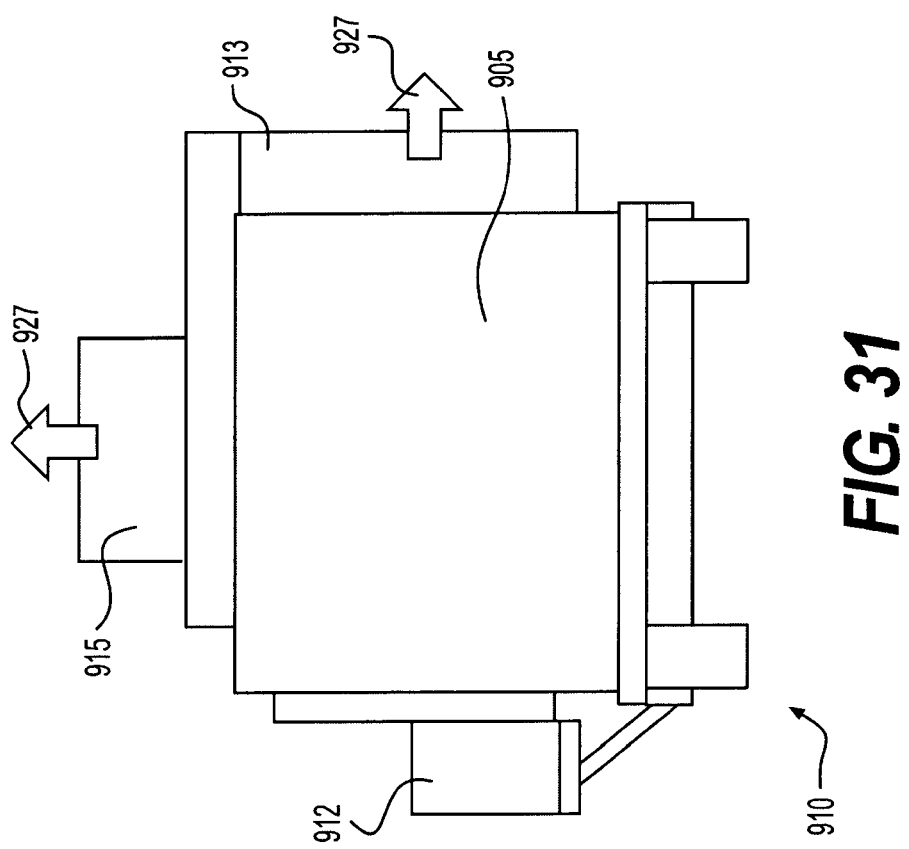
Figure 32:
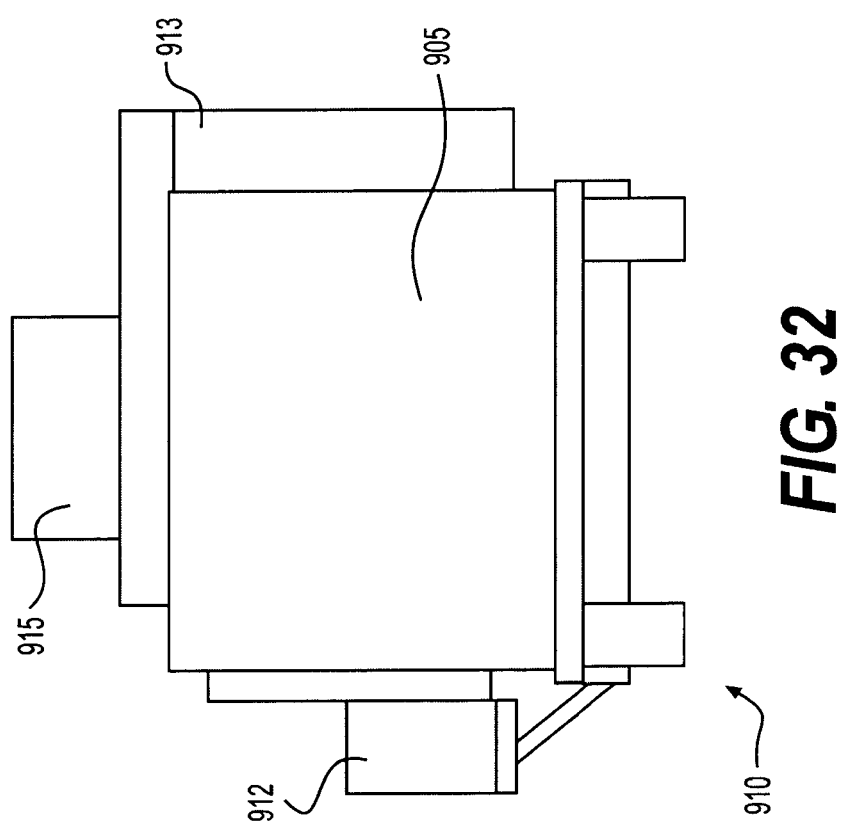
Figure 33:
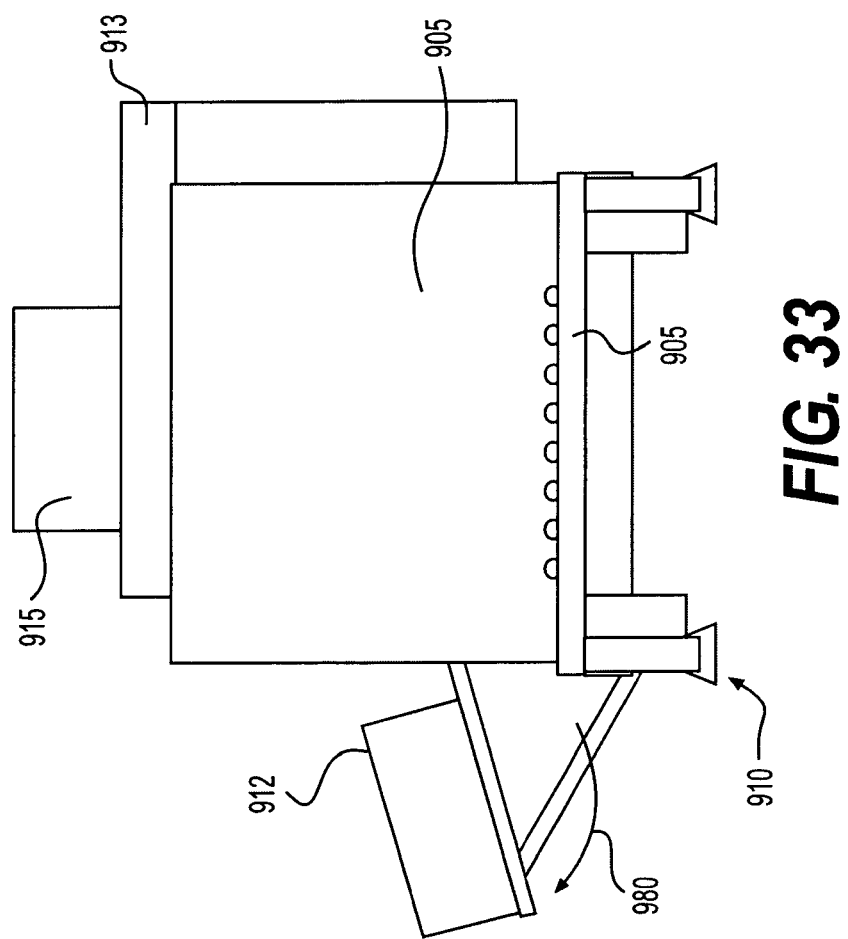
Figure 34:
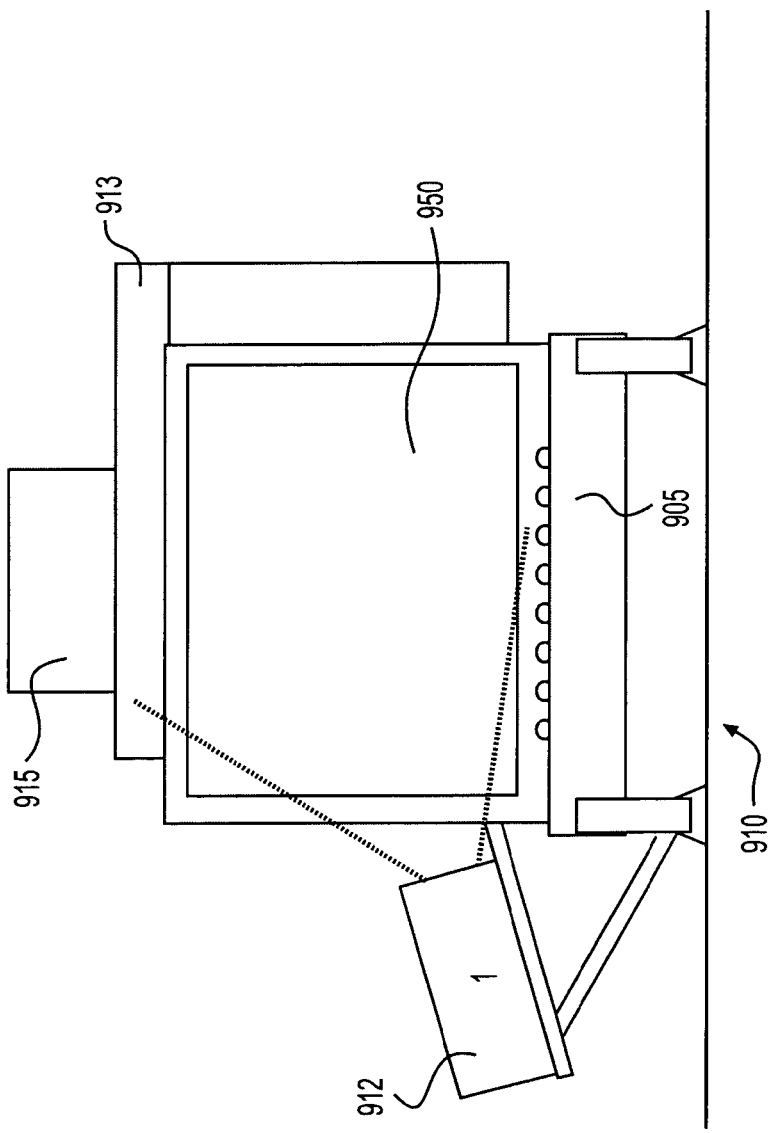
Figure 35:
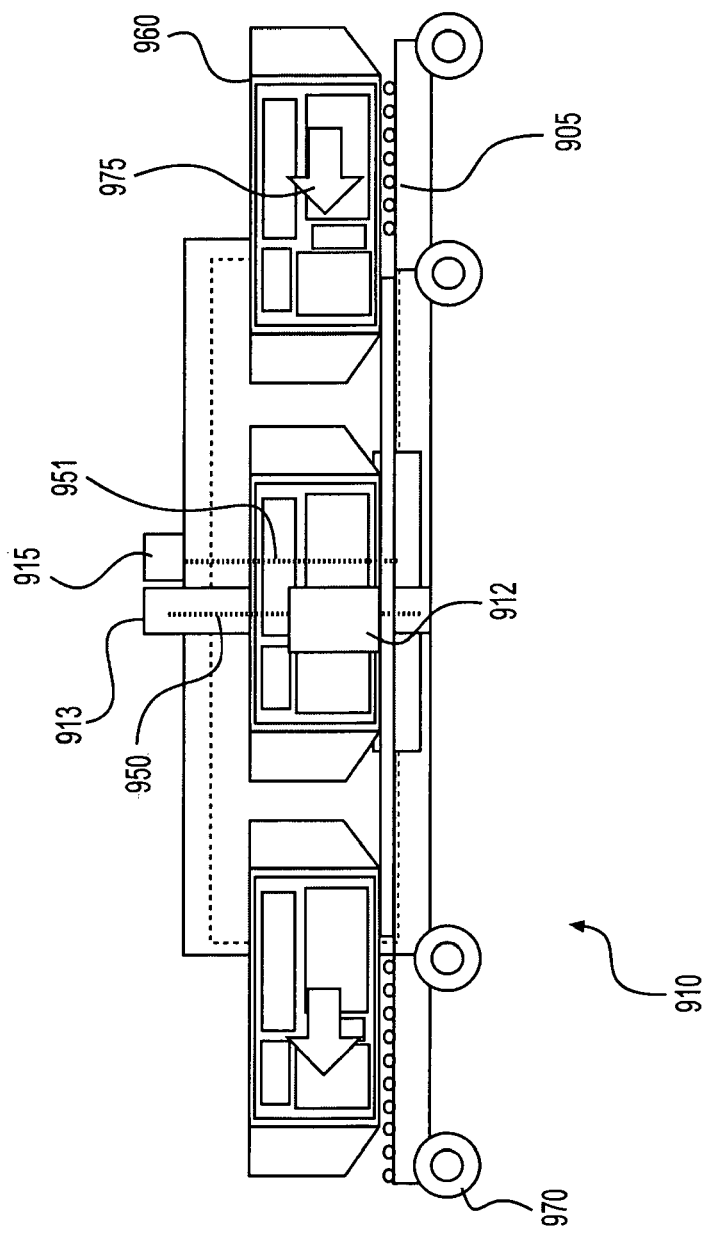

FIGS. 28-35 depict views of a trailer-based inspection system 910 consistent with an embodiment of the present disclosure. FIG. 28 depicts the trailer-based inspection system 910 configured for transportation, such as on a flat bed truck (not shown). The position of a side a scanner 912, a top scanner 915, a side detector 913, a scanning chamber 905, and a conveyor bed 906 are shown. In addition, wheels 970 are depicted as stored for transportation. FIG. 29 shows a further configuration where a vehicle may tow the trailer-based inspection system 910. In the configuration depicted in FIG. 29, the wheels 970 are in position to allow the trailer-based inspection system 910 to be moved about easily. The side scanner 912 can be stowed in the vicinity of the side detector 913 and the top scanner 915. FIG. 30 is an alternate view of the transportation configuration depicted in FIG. 29. FIGS. 31 and 32 depict a translation of the side detector 913 and the top scanner 915 (in the direction of arrows 927) as the trailer-based inspection system 910 is configured for scanning. FIG. 33 depicts the side scanner 912 being rotated (as indicated by arrow 980) so that it is in position for scanning. FIGS. 34 and 35 depict the trailer-based inspection system 910 in scanning configuration. For example, FIG. 35 depicts containers 960, and also depicts the relative position of a scanning region 950 (associated with the side scanner 912) and a scanning region 951 (associated with the top scanner 915).

Advantages of these trailer-based inspection systems 710, 810, and 910 as disclosed herein include rapid deployment, conveyance scanning, image management and decision-making, and rapid stowing to enable minimum time lag between uses at different locations. Additional features of the trailer-based embodiments include low height ease of use on flight lines and in cargo buildings; rapid deployment, use and stowing; on-board power, scan-taking, image analysis, mission-required radiation; scanning mechanism will rotate into place and operate in a perpendicular position to the airplane; dual scanner design provides two simultaneous, yet independent views of the conveyance; and optimum configuration for OCR, camera array and other mission-useful tools.

INDUSTRIAL APPLICABILITY

The disclosed system and method can be applicable to detection of objects and materials of interest using an automated or semi-automated process. Although disclosed embodiments are described in association with container, crate, truck or cargo pallet inspection such as at an airport, train station, cargo inspection or other port applications, the disclosed inspection system and inspection method can be used in other applications, such as medical imaging in a hospital or imaging facility, product quality control in a factory, etc.

It will be apparent to those skilled in the art that various modifications and variations can be made in the disclosed system and method without departing from the scope of the disclosure. Additionally, other embodiments of the disclosed system and method will be apparent to those skilled in the art from consideration of the specification. It is intended that the embodiments disclosed in the specification be considered as examples only, with a true scope of the disclosure being indicated by the following claims and their equivalents.

What is claimed is:

1. A system for scanning an object of interest, the system comprising:
    a controller for generating scan instructions;
    a scanner, responsive to the scan instructions, for providing radiation at an energy to generate scan data for the object of interest;
    an other scanner, responsive to the scan instructions, for providing radiation at an other energy to generate other scan data for the object of interest;
    a conveyance controller for generating conveyance instructions to control the relative movement of the scanner and the other scanner with respect to the object of interest based on the scan data and the other scan data; and
    a conveyor, responsive to the conveyance instructions, configured to impart the relative movement of the scanner and the other scanner with respect to the object of interest;
    wherein the controller is configured to receive object information and to generate the scan instructions based at least in part on the received object information; and
    wherein the received object information includes at least one of weight distribution information of the object of interest and density distribution information of the object of interest.

2. The system of claim 1, wherein the controller generates other scan instructions based upon the scan data and the scanner is responsive to the other scan instructions, and the other scanner is responsive to the other scan instructions.

3. The system of claim 1, wherein at least one of the scanner and the other scanner comprise at least one detector of a set of detectors consisting of: a stereoscopic gamma radiation detector, a passive gamma radiation detector, and a passive neutron detector.

4. The system of claim 1, wherein the controller is configured to:
define a minimum x-ray penetration of the object of interest,
determine an x-ray penetration of the object of interest, and
determine if the x-ray penetration is lower than the minimum x-ray penetration.

5. The system of claim 4, wherein the other scan instructions are based at least in part on the x-ray penetration of the object of interest.

6. The system of claim 4, wherein the conveyance controller is configured to generate the conveyance instructions based at least in part on the x-ray penetration of the object of interest.

7. The system of claim 1, wherein the scan data is used to produce a radiographic image for display.

8. The system of claim 1, wherein the conveyance controller is configured to receive the object information and to generate the conveyance instructions based at least in part on the received object information.

9. The system of claim 8, wherein the object information further includes at least one data type of a set of data types consisting of: information of a type of material of the object of interest, origin information, destination information, routing information, or manifest information associated with the object of interest.

10. The system of claim 1, wherein the conveyance controller is configured to determine the at least one of the weight distribution information and the density distribution information.

11. A system configured to scan an object of interest, the system comprising:
a controller that generates scan instructions based at least in part on non-scan-based input data and generates other scan instructions based on scan data;
a scanner, responsive to the scan instructions, for providing radiation at an energy to the object of interest, and for generating the scan data associated with the object of interest;
wherein the scanner, responsive to the other scan instructions, provides radiation at an other energy to the object of interest;
a conveyance controller for generating conveyance instructions based at least in part on the input data and generates other conveyance instructions based on the scan data,
wherein the conveyance instructions and the other conveyance instructions define a relative movement between the scanner and the object of interest; and
a conveyor, responsive to the conveyance instructions and the other conveyance instructions, configured to impart the relative movement between the scanner and the object of interest;
wherein the non-scan-based input data includes at least one data type of a set of data types consisting of: information of a type of material of the object of interest, origin information, destination information, routing information, and manifest information associated with the object of interest.

12. The system of claim 11, wherein the scan instructions and the other scan instructions are the same.

13. The system of claim 11, wherein the conveyance instructions and the other conveyance instructions are the same.

14. The system of claim 11, wherein the scanner includes a high energy scanner and a low energy scanner.

15. The system of claim 11, wherein the scanner comprises at least one detector of a set of detectors consisting of: a stereoscopic gamma radiation detector, a passive gamma radiation detector, and a passive neutron detector.

16. The system of claim 11, wherein the controller is configured to:
define a minimum x-ray penetration of the object of interest,
determine an x-ray penetration of the object of interest, and
determine if the x-ray penetration is lower than the minimum x-ray penetration.

17. The system of claim 16, wherein the controller is configured to generate the other scan instructions based at least in part on the x-ray penetration of the object of interest.

18. The system of claim 16, wherein the conveyance controller is configured to generate the other conveyance instructions based at least in part of the x-ray penetration of the object of interest.

19. A non-transitory computer-readable medium storing a program that, when executed by a processor, performs a method of scanning an object of interest, the method comprising:
receiving object information;
generating scan instructions;
generating conveyance instructions;
providing radiation to an object of interest using a scanner at an energy in response to the scan instructions and the conveyance instructions;
acquiring scan data;
evaluating the scan data and generating other scan instructions and other conveyance instructions based on the scan data;
providing radiation to the object of interest using the scanner at an other energy in response to the other scan instructions; and
imparting relative movement between the scanner and the object of interest using a conveyor in response to the conveyance instructions and the other conveyance instructions;
wherein the generated scan instructions are based at least in part on the received object information; and
wherein the received object information includes at least one of weight distribution information of the object of interest and density distribution information of the object of interest.

20. The non-transitory computer-readable medium of claim 19, wherein the scanner includes a high-energy scanner and a low-energy scanner.

21. The non-transitory computer-readable medium of claim 19, wherein the conveyance instructions and the other conveyance instructions include instructions that define a relative motion between the object of interest and the scanner and where the relative motion between the object of interest and the scanner includes maintaining the scanner substantially stationary relative to a geographic location and moving the object of interest relative to the geographic location.

22. The non-transitory computer-readable medium of claim 19, wherein the conveyance instructions and the other conveyance instructions include instructions that define a relative motion between the object of interest and the scanner and where the relative motion between the object of interest and the scanner includes maintaining the object of interest substantially stationary relative to a geographic location and moving the scanner relative to the geographic location.

23. The non-transitory computer-readable medium of claim 19, wherein evaluating the scan data includes:
   defining a minimum x-ray penetration of the object of interest,
   determining an x-ray penetration of the object of interest based upon the scan data, and
   determining if the x-ray penetration is lower than the minimum x-ray penetration.

24. The non-transitory computer-readable medium of claim 19, the method of scanning an object of interest further comprising:
   generating a radiographic image for display based on the scan data.

25. The non-transitory computer-readable medium of claim 24, the method of scanning an object of interest further comprising:
   updating the radiographic image based on other scan data acquired by the other scanner at the other energy in response to the other scan instructions.

26. The non-transitory computer-readable medium of claim 24, wherein evaluating the scan data further includes:
   discrimination analysis of the radiographic image to identify at least a portion of the radiographic image associated with an item of interest.

27. The non-transitory computer-readable medium of claim 26, wherein evaluating the scan data further includes:
   shape and pattern analysis on at least part of the scan data.

28. The non-transitory computer-readable medium of claim 24, wherein evaluating the scan data further includes:
   shape and pattern analysis on at least part of the scan data.

29. The non-transitory computer-readable medium of claim 28, wherein evaluating the scan data further includes:
   determining, using the shape and pattern analysis, if the scan data is inconsistent with the received object information.

30. The non-transitory computer-readable medium of claim 19, wherein evaluating the scan data includes:
   determining a material discrimination value based at least in part on the scan data.

31. The non-transitory computer-readable medium of claim 19, wherein evaluating the scan data further includes:
   determining if the scan data is inconsistent with the received object information.

* * * * *

UNITED STATES PATENT AND TRADEMARK OFFICE
CERTIFICATE OF CORRECTION

PATENT NO. : 10,228,334 B2
APPLICATION NO. : 13/577060
DATED : March 12, 2019
INVENTOR(S) : Kristofer J. Roe, Timothy S. Norton and Nicolas Dumay Page 1 of 1

It is certified that error appears in the above-identified patent and that said Letters Patent is hereby corrected as shown below:

On the Title Page

Item (57), Line 8 of ABSTRACT, "for providing radiation an at other energy to generate" should read --for providing radiation at an other energy to generate--.

Signed and Sealed this
Seventh Day of May, 2019

Andrei Iancu
*Director of the United States Patent and Trademark Office*